US011806352B2

(12) United States Patent
Draijer et al.

(10) Patent No.: US 11,806,352 B2
(45) Date of Patent: Nov. 7, 2023

(54) THEOBROMINE FOR INCREASING HDL-CHOLESTEROL

(75) Inventors: Richard Draijer, AT Vlaardingen (NL); Bert-Jan Hendrik Van Den Born, AT Vlaardingen (NL)

(73) Assignee: UPFIELD EUROPE B.V., Rotterdam (NL)

( * ) Notice: Subject to any disclaimer, the term of this patent is extended or adjusted under 35 U.S.C. 154(b) by 0 days.

(21) Appl. No.: 13/697,578

(22) PCT Filed: May 16, 2011

(86) PCT No.: PCT/EP2011/057816
§ 371 (c)(1),
(2), (4) Date: Dec. 4, 2012

(87) PCT Pub. No.: WO2011/144545
PCT Pub. Date: Nov. 24, 2011

(65) Prior Publication Data
US 2013/0116221 A1 May 9, 2013

(30) Foreign Application Priority Data
May 19, 2010 (EP) .................... 10163276

(51) Int. Cl.
| A61K 31/522 | (2006.01) |
| A61K 31/56 | (2006.01) |
| A61K 45/06 | (2006.01) |
| A23L 33/105 | (2016.01) |
| A23L 33/12 | (2016.01) |
| A23L 33/11 | (2016.01) |

(52) U.S. Cl.
CPC .......... *A61K 31/522* (2013.01); *A23L 33/105* (2016.08); *A23L 33/11* (2016.08); *A23L 33/12* (2016.08); *A61K 31/56* (2013.01); *A61K 45/06* (2013.01); *A23V 2002/00* (2013.01)

(58) Field of Classification Search
CPC ........ A23V 2002/00; A23V 2200/3262; A23V 2250/21; A23V 2250/1868; A23V 2250/187; A23V 2250/2136; A61K 2300/00; A61K 31/522; A61K 31/56; A61K 45/06; A23L 33/105; A23L 33/11; A23L 33/12; A61P 9/10
See application file for complete search history.

(56) References Cited

U.S. PATENT DOCUMENTS

| 1,073,444 A | 9/1913 | Riddle |
| 1,855,026 A | 4/1932 | Livingston |
| 1,925,326 A | 9/1933 | Kellogg et al. |
| 2,524,291 A | 10/1950 | Hoffman |
| 2,645,580 A | 7/1953 | Schultz |
| 2,954,293 A | 9/1960 | Rusoff |
| 3,528,819 A | 9/1970 | Hamilton et al. |
| 3,753,726 A | 8/1973 | Clinton et al. |
| 4,183,965 A | 1/1980 | Mookherjee et al. |
| 4,244,977 A | 1/1981 | Kahn et al. |
| 4,315,036 A | 2/1982 | Husaini et al. |
| 4,542,035 A | 9/1985 | Huang et al. |
| 4,904,733 A | 2/1990 | Gerth et al. |
| 4,904,773 A | 2/1990 | Yu et al. |
| 4,963,372 A | 10/1990 | Zumbe |
| 5,112,827 A | 5/1992 | Saunders et al. |
| 5,338,554 A | 8/1994 | Vogt et al. |
| 5,562,941 A | 10/1996 | Levy |
| 6,156,371 A | 12/2000 | Vareille et al. |
| 6,174,555 B1 | 1/2001 | Leas et al. |
| 6,290,994 B1 | 9/2001 | Lazaro Flores et al. |
| 6,305,275 B2 | 10/2001 | Grassler et al. |
| 6,312,753 B1 | 11/2001 | Kealey et al. |
| 6,352,734 B1 | 3/2002 | Martin, Jr. et al. |
| 7,115,285 B2 | 10/2006 | McKee et al. |
| 7,465,468 B1 | 12/2008 | Cheney et al. |
| 2001/0000889 A1 | 7/2001 | Subbiah |
| 2002/0172732 A1 | 11/2002 | Ter Laak et al. |
| 2002/0192316 A1 | 12/2002 | Altaffer et al. |
| 2003/0003212 A1 | 1/2003 | Chien et al. |
| 2003/0008046 A1 | 1/2003 | Gerlat et al. |
| 2003/0013729 A1 | 1/2003 | Iqbal et al. |
| 2003/0064501 A1 | 4/2003 | Yamamoto et al. |
| 2003/0065020 A1 | 4/2003 | Gale et al. |
| 2003/0176493 A1 | 9/2003 | Romanczyk, Jr. et al. |
| 2003/0229083 A1 | 12/2003 | Debnath et al. |
| 2004/0005347 A1 | 1/2004 | Ter Laak et al. |
| 2004/0077556 A1 | 4/2004 | Chinery |

(Continued)

FOREIGN PATENT DOCUMENTS

| CN | 1094897 | 11/1994 |
| CN | 101028265 | 9/2007 |

(Continued)

OTHER PUBLICATIONS

Mumford et al, Psychopharmacology (1994) 115: 1-8.*
Mayo Clinic , 2012.*
Lab Tests Online, Aug. 26, 2013.*
Cholesterol Information, Continuing Medical Implementation® Inc. Nov. 2007 (Year: 2007).*
Eteng et al, National Research, vol. 20, No. 10, pp. 1513-1517, 2000. (Year: 2000).*
EFSA, The EFSA Journal (2008) 725, 1-66 (Year: 2008).*
J.H. et al., Can. J. Physiol. Pharmacol. 75: 217-227 (1997). (Year: 1997).*

(Continued)

*Primary Examiner* — Jean P Cornet
(74) *Attorney, Agent, or Firm* — ARENTFOX SCHIFF LLP

(57) ABSTRACT

Theobromine for use in the treatment of increasing HDL-cholesterol and/or increasing the ratio HDL-cholesterol:LDL-cholesterol in humans and the use of theobromine for increasing HDL-cholesterol in humans, and/or for increasing the ratio HDL-C/LDL-C, and compositions comprising theobromine.

17 Claims, No Drawings

(56) References Cited

U.S. PATENT DOCUMENTS

| | | |
|---|---|---|
| 2004/0198754 A1 | 10/2004 | McKee et al. |
| 2004/0202726 A1 | 10/2004 | DeShay |
| 2005/0031762 A1 | 2/2005 | McCarthy et al. |
| 2005/0069625 A1 | 3/2005 | Chimel et al. |
| 2005/0089584 A1 | 4/2005 | Gow et al. |
| 2005/0096331 A1 | 5/2005 | Das et al. |
| 2005/0113368 A1 | 5/2005 | Bhuniya et al. |
| 2006/0134294 A1 | 6/2006 | McKee et al. |
| 2007/0014834 A1 | 1/2007 | McDowall et al. |
| 2007/0042102 A1 | 2/2007 | Furcich |
| 2007/0207188 A1 | 9/2007 | Miller et al. |
| 2007/0219146 A1 | 9/2007 | Bhaskaran et al. |
| 2008/0014331 A1 | 1/2008 | Badalov |
| 2008/0226786 A1 | 9/2008 | Ward et al. |
| 2008/0233245 A1 | 9/2008 | White et al. |
| 2009/0012156 A1* | 1/2009 | Draijer ............... A23L 2/52 514/456 |
| 2009/0110774 A1 | 4/2009 | Milici |
| 2009/0263556 A1 | 10/2009 | Blondeel et al. |
| 2009/0297687 A1 | 12/2009 | Ramirez Marco et al. |
| 2010/0166933 A1 | 7/2010 | Berry et al. |
| 2010/0166938 A1 | 7/2010 | Hoddle |
| 2011/0003834 A1 | 1/2011 | Hanamura et al. |
| 2011/0086138 A1 | 4/2011 | Jia et al. |
| 2011/0318474 A1 | 12/2011 | Berry et al. |
| 2013/0052280 A1 | 2/2013 | Draijer et al. |
| 2013/0116221 A1 | 5/2013 | Draijer et al. |

FOREIGN PATENT DOCUMENTS

| | | |
|---|---|---|
| EP | 0147483 | 7/1985 |
| EP | 0220836 | 5/1987 |
| EP | 0325916 A1 | 1/1989 |
| EP | 0416718 A2 | 3/1991 |
| EP | 0795273 | 9/1997 |
| EP | 1061006 | 12/2000 |
| EP | 0795273 | 10/2001 |
| EP | 1219698 A1 | 3/2002 |
| EP | 1201135 A1 | 5/2002 |
| EP | 1364584 | 11/2003 |
| EP | 1366672 | 12/2003 |
| EP | 0760240 | 10/2005 |
| EP | 1383537 | 6/2006 |
| EP | 1787527 | 6/2007 |
| EP | WO2007098205 A2 | 8/2007 |
| EP | 1856988 A1 | 11/2007 |
| EP | 2022344 A1 | 11/2009 |
| EP | 2108270 | 3/2011 |
| EP | 2253567 | 7/2013 |
| ES | 2166725 | 4/2002 |
| ES | 2166725 A | 4/2002 |
| GB | 758712 | 10/1956 |
| GB | 1106728 | 3/1968 |
| GB | 1157919 | 7/1969 |
| GB | 2019187 | 10/1979 |
| GB | 2185376 A | 7/1987 |
| GB | 2364503 | 1/2002 |
| JP | 58162260 | 9/1983 |
| JP | 256428 | 2/1990 |
| JP | 08168343 | 7/1996 |
| JP | 08-298930 | 11/1996 |
| JP | 08298930 | 11/1996 |
| JP | 09205991 | 8/1997 |
| JP | 09205991 A | 8/1997 |
| JP | 10004919 | 1/1998 |
| JP | 10248501 | 9/1998 |
| JP | 2001169753 | 6/2001 |
| JP | 2004057153 | 2/2004 |
| JP | 2005013127 | 1/2005 |
| JP | 2005047839 | 2/2005 |
| JP | 2005348656 | 12/2005 |
| JP | 2006151878 | 6/2006 |
| JP | 2006282576 | 10/2006 |
| JP | 2007006853 | 1/2007 |
| JP | 2007284458 | 11/2007 |
| JP | 2008167747 | 7/2008 |
| JP | 2008291002 | 12/2008 |
| SU | 1637740 A1 | 3/1991 |
| WO | WO9601568 | 1/1996 |
| WO | WO9632113 | 10/1996 |
| WO | WO9740700 | 11/1997 |
| WO | WO9804144 | 2/1998 |
| WO | WO9813023 | 4/1998 |
| WO | WO9904211 | 1/1999 |
| WO | WO9908681 | 2/1999 |
| WO | WO9942111 | 8/1999 |
| WO | WO0106865 | 2/2001 |
| WO | WO0111988 A2 | 2/2001 |
| WO | WO 0117494 A1 * | 3/2001 |
| WO | WO02081454 | 10/2002 |
| WO | WO02100192 | 12/2002 |
| WO | WO03043433 | 5/2003 |
| WO | WO03096821 | 11/2003 |
| WO | WO2003090673 | 11/2003 |
| WO | WO04082609 | 9/2004 |
| WO | WO 2004082609 A2 * | 9/2004 |
| WO | WO2004093571 | 11/2004 |
| WO | WO06067866 | 6/2006 |
| WO | WO06106023 | 10/2006 |
| WO | WO07003527 | 1/2007 |
| WO | WO2007030570 | 3/2007 |
| WO | WO2007042745 A1 | 4/2007 |
| WO | WO2007106473 | 9/2007 |
| WO | WO2007011892 | 10/2007 |
| WO | WO2007109884 | 10/2007 |
| WO | WO2007122251 A2 | 11/2007 |
| WO | WO07146306 | 12/2007 |
| WO | WO9802165 | 1/2008 |
| WO | WO08059064 A1 | 5/2008 |
| WO | WO2008059064 A1 | 5/2008 |
| WO | WO2008125380 | 10/2008 |
| WO | WO2009015996 | 2/2009 |
| WO | WO2009099221 | 8/2009 |
| WO | WO2009140784 | 11/2009 |
| WO | WO2011095389 A1 | 8/2011 |

OTHER PUBLICATIONS

Hoskins et al., Future Lipidol. (2006) 1(5), 579-591 (Year: 2006).*
Ocamor® product specification, accessed on Feb. 23, 2021 (Year: 2021).*
Baba et al., J. Nutr. 137: 1436-1441, 2007. (Year: 2007).*
Xocai activ, Internet Xocai activ 2010 p. 1-4.
Alnatura Glucks-Tee test and price comparison, Alnatura Glucks-Tee Internet Citation 2006 pp. 1-5 Translation.
De Centrale Commissie Mensgebonden Onderzoek, De Centrale Commissie Mensgebonden Onderzoek 2008 pp. 1-7.
Nutritional Values of Dark Chocolate and Cocoa Powder, USDA National Nutrient Database for Standard Reference 2008 pp. 1-4, USDA.
Picard Best chocolat, 2005 pp. 1-2 Translation, XP-002569867.
Abdou et al., Relaxation and immunity enhancement effects of γ-Aminobutyric acid (GABA) administration in humans, BioFactors, May 27, 2006, 201-208, 26, IOS Press.
Adam, How ice cream tickles your brain, The Guardian, Apr. 29, 2005.
Anonymous, 4 Best chocolat 70% de cacao-feves de cacao, Picard 4 Best chocolat 70% de cacao-feves de cacao, Feb. 22, 2010, p. 1-3, XP002569868.
Anonymous, Dark Chocolate Ice Cream with Cocoa Nibs, Coconut & Lime Recipes, Apr. 23, 2005, p. 1-3 XP-002516346.
Bergen et al., Comparative aspects of lipid metabolism: Impact on contemporary research and use of animal models, The Journal of Nutrition 2005 pp. 2499-2502.
Buijsse et al., Cocoa Intake, Blood Pressure, and Cardiovascular Mortality, Arch Intern Med, Feb. 27, 2006, 411-417, 166.
Cienfuegos-Jovellanos et al., Antihypertensive Effect of a Polyphenol-Rich cocoa Powder Indistrially Processed To Preserve the Original Flavonoids of the Cocoa Beans, J. Agric. Food Chem, 2009, 6156-6162.

(56) References Cited

OTHER PUBLICATIONS

Drewnowski, The Science and Complexity of Bitter Taste, Nutrition Reviews 2001 vol. 59 No. 6 pp. 163-169 XP009120025.
Eteng et al, Comparative Effects of Theobromine and Cocoa Extract on Lipid Profile in Rats, Nutrition Research, Oct. 1, 2000, 1513-1517, vol. 20 No 10.
Eteng et al., Caffeine and theobromine levels in selected Nigerian beverages, Plant Foods for Human Nutrition, Oct. 12, 1999, 337-344, 54, Kluwer Academic Publlishers.
Graham, Green Tea Composition, Consumption, and Polyphenol Chemistry, Preventive Medicine 1992 21 pp. 334-350, Academic Press, Inc.
Hayashi et al., Binding Energy of Tea Catechin/Caffeine Complexes in Water Evaluated by Titration Experiments with 1H-NMR, Biosci Biotechnol Biochem 2004 68 (12) pp. 2512-2518.
Henry et al., Reduction of chronic psychosocial hypertension in mice by decaffeinated tea, Hypertension 1984 6 pp. 437-444.
Vitic et al., Comparative studies of the serum lipoproteins and lipids in some domestic, laboratory and wild animals, Animal serum lipoproteins and lipids, Comp Biochem Physiol., 1993, 106B No. 1, pp. 223-229.
John M. Dietschy et al., Role of liver in the maintenance of cholesterol and low density lipoprotein homeostasis in different animal species, including humans, pp. 1637-1659, 34, 1993, Journal of Lipid Research.
Johnston et al., Modulation of ionotropic GABA Receptors by Natural Products of Plant Origin, Advances in Pharmacology 2006 vol. 54 pp. 285-316, Elsevier Inc.
Kattenberg et al., For a naturally fresh flavour, Food Science & Technology, 2001, 28-30, 15(4).
Khan et al, Regular consumption of cocoa powder with milk increases HDL cholesterol and reduces oxidized LDL levels in subjects at high-riskof cardiovascular disease, Nutrion Metabolism & Cardiovascular Diseases, Feb. 1, 2011, 1-8.
Kris-Etherton et al, Design criteria for studies examining individual fatty acid effects on cardiovascular disease risk factors: human and animal studies, pp. 1590S-1596S, 1997; 65, The American Journal of Clinical Nutrition.
Laurent et al, Recent advances in arterial stiffness and wave reflection in human hypertension, Hypertension 2007 vol. 49 No. 6 pp. 1202-1206.
London, Arterial compliance central aortic blood pressure and ACE inhibition, Medicographia, Jan. 1, 2009, 32-37, 31, No. 1, FR.
Nakamura et al, Beneficial Potential of Casein Hydrolysate containing Val-Pro-Pro on Central Blood Pressure, Journal of Medical Food, Dec. 2009, 1221-1226, vol. 12 No. 6.
Pascual et al, Cacao y chocolate: un placer cardiosaludable?, Clinica E Investigacion en Arteriosclerosis, Aug. 2009, 198-209, vol. 21 No. 4.
Peleg et al., Bitterness and astringency of flavan-3-ol monomers, dimers and trimers, Journal of the Science of Food and Agriculture 1999 79 pp. 1123-1128.
Smit et al., Methylxantines are the psycho-pharmacologically active constituents of chocolate, Psychopharmacology, May 5, 2004, 412-419, 176, Springer-Verlag.
Szejtli, Cyclodextrins in Food, Cosmetics and Toiletries, Starke 34 1982 Nr 11 pp. 379-385, Verlag Chemie GmbH, Weinheim.
Telles, Mood foods: Dancing to a merry tune, Frost & Sullivan Market Insight, Feb. 18, 2008, 1-2, Frost & Sullivan, US.
Van Den Bogaard et al., Differential Effect of Cocoa Drinks with Low & High Theobromine Dose on Peripheral & Central Blood Pressure, Poster from European Society of Hypertension Meeting 2010 p. 1.
Vlachopoulos et al, Effects of nutrition on arterial rigidity and reflected waves, Sang Thrombose Vaisseaux, Nov. 2007, 479-486, vol. 19 No. 9.
Vlachopoulos et al., Relation of Habitual Cocoa Consumption to Aortic Stiffness and Wave Reflections and to Central Hemodynamics in Healthy Individuals, American Journal of Cardiology 2007 vol. 99 No. 10 pp. 1473-1475.
Wei et al., Study on inclusion complex of cyclodextrin with methyl xanthine derivatives by fluorimetry, Spectrochimica Acta Part A 59 pp. 2697-2703, Jan. 13, 2003.
Werner G. Bergen et al., Recent Advances in Nutritional Sciences, Comparative Aspects of Lipid Metabolism Impact on Contemporary Research and Use of Animal Models, pp. 2499-2502, 05, 2005, The Journal of Nutrition.
Winston J. Craig et al., Caffeine and Tehobromine Levels in Cocoa and Carob Products, Journal of Food Science, Jan. 1984, 302-303, vol. 49, Issue 1.
Co-pending application Berry et al., U.S. Appl. No. 12/639,442, filed Dec. 16, 2009.
Co-pending application Hoddle, U.S. Appl. No. 12/639,468, filed Dec. 16, 2009.
How To Make Ice Cream, 5 Ways To Make Ice Cream, Mar. 2014, pp. 1-7.
Chocolate Ganache Cake, Betty Crocker, Feb. 2009, 1-13http://www.bettycrocker.com/recipes/chocolate-ganache-cake/7a48c634-5bf2-427c-aa73-32a83066251b?.
Drinking Chocolate Recipe, Drinks Mixer, Jun. 4, 2003, 1-2. First Published Jun. 4, 2003 as per AU2009248450 B8.
Food Standards Agency Information Bulletin on Methods of Analysis and Sampling for Foodstuffs, Food Standards Agency, Feb. 2006, 1-91, 63.
General Nutrition Information Well-being made simple, The Hershey Company Chocolate and Nutrition Facts and Information, Oct. 13, 2005, 1-4.
Plasma LDL and HDL Cholesterol and Oxidized LDL Concentrations Are Altered in Normoand Hypercholesterolemic Humans after Intake of Different Levels of Cocoa Powder, The Journal of Nutrition, Jan. 1, 2007, 1436-1441, 137.
Search Report in CN200910266700, Search Report in CN200910266700 (Translation), dated Aug. 31, 2012.
Elvers et al, Margarines and shortenings, Ullmanns Encyclopedia of Industrial Chemistry, 1990, 156-158, 5th Edition, vol. A16.
Gao Yunhua,, "Cocoa", Wine and Rectification, "Cocoa", Wine and Rectification pp. 220, Aug. 31, 1999, 220, ., China Logistics Publishing House, CN.
Gilbert et al., Caffeine Content of Beverages as Consumed, CMA Journal, Feb. 7, 1976, pp. 205-208, vol. 114.
Ian Knight, Chocolate & Cocoa Health and Nutrition, Chocolate & Cocoa, 1999, 153-173.
IPR2 in PCTEP2011057816, dated Sep. 6, 2012.
Kathie Smith, Cooking with coffee: Ingredient adds flavor to an array of entrees, desserts, and drinks, The Blade. Com, 2004, pp. 1-3http://www.toledoblade.com/Food/2004/09/21/Cooking-with-coffee-Ingredient-adds-flavor-to-an-array-of-entrees-desserts-and-drinks.html, ., The Blade.
Sai Na, The Source of Charm of Chocolate, Fall in Love with Chocolate, The Source of Charm of Chocolate, Fall in Love with Chocolate, Jan. 31, 2004, 74, ., China Astronautic Publishing Co., Ltd,, CN.
Search Report in EP10163276, dated Sep. 1, 2010.
Search Report in PCTEP2011057816, dated Jul. 11, 2011.
Written Opinion in PCTEP2011057816, dated Jul. 11, 2011.
Written Report in EP10163276, dated Sep. 1, 2010.
Yokogoshi et al., The Hypercholesterolemic Effect of Caffeine-Containing Beverages and Xanthine-Derivatives in Rats, Nutrition Reports International, Oct. 1, 1983, 805-814, 28.
Abdi et al., Placental transfer and foetal disposition of caffeine and its immediate metabolites in the 20-day pregnant rate: function of dose, Xenobiotica, 1992, pp. 449-456, vol. 23 No. 4.
Theobromine, Wikipedia, 2015, pp. 1-10.
Abdi et al., Placental transfer adn foetal disposition of caffeine and its immediate metabolites in the 20-day pregnant rate: function of dose, Xenobiotica, 1992, pp. 449-456, vol. 23 No. 4.
Actis-Goretta et al., Inhibition of Angiotensin Converting Enzyme Activity by Flavanol-Rich Foods, Journal of Agricultural and Food Chemistry, 2006, pp. 229-234, vol. 54, No. 1.
Azra Mahmud and John Feely, Acute Effect of Caffeine on Arterial Stiffness and Aortic Pressure Waveform, Hypertension, 2001, pp. 227-231, 38.

(56) References Cited

OTHER PUBLICATIONS

Balzer et al., Sustained Benefits in Vascular Function Through Flavanol-Containing Cocoa in Medicated Diabetic Patients, Journal of the American College of Cardiology JACC, 2008, pp. 2141-2149, vol. 51, No. 22.
Baron et al., Hemodynamic and Electrophysiologic Effects of Acute Chocolate Ingestion in Young Adults, American Journal of Cardiology, Mar. 15, 1999, pp. 370-373, 84.
Beltman, et al., Predictive value of ambulatory blood pressure shortly after withdrawal of antihypertensive drugs in primary care patients, The BMJ, Aug. 17, 1996, pp. 404-406, 313.
Bonati et al., Caffeine disposition after oral doses, Clinical Pharmacology & Therapeutics, Jul. 1, 1982, pp. 98-106, v. 32, No. 1, IT.
Bonati et al., I. Kinetics and Metabolism of the Theobromine in Male Rats, Toxicology, 1984, pp. 327-341, 30.
Bonetti et al., Noninvasive Identification of Patients With Early Coronary Atherosclerosis by Assessment of Digital Reactive Hyperemia, Journal of the American College of Cardiology, 2004, pp. 2137-2141, vol. 44 No. 11.
Brusick et al., Genotoxicity of cocoa in a series of short-term assays, Mutation Research, 1986, pp. 115-121, 169.
Buijsse et al., Chocolate consumption in relation to blood pressure and risk of cardiovascular disease in German adults, European Heart Journal, 2010, pp. 1616-1623, 31.
Campbell et al., Activity Assays and Immunoassays for Plasma Renin and Prorenin: Information Provided and Precautions Necessary for Accurate Measurement, Clinical Chemistry, 2009, pp. 867-877, 55-5.
Carney et al., Differential Antagonism of the Behavioral Depressant and Hypothermic Effects of 5' -(N-ethylcarboxamide) Adenosine by Theobromine, Pharmacology Biochemistry & Behavior, Apr. 8, 1986, pp. 769-773, 25.
Chen et al., Estimation of Central Aortic Pressure Waveform by Mathematical Transformation of Radial Tonometry Pressure. Validation of Generalized Transfer Function, Circulation, Apr. 1, 1997, pp. 1827-1836, vol. 95 No. 7.
Chobanian et al., The Seventh Report of the Joint National Committee on Prevention, Detection, Evaluation, and Treatment of High Blood Pressure, Journal of American Medical Association, 2003, pp. 2560-2572, 289-19.
Cifkova et al., Practice Guidelines for Primary Care Physicians: 2003 ESH/ESC Hypertension Guidelines, Journal of Hypertension, 2003, pp. 1779-1786, vol. 21 No. 10.
Cook et al., Implications of Small reductions in Diastolic Blood Pressure for Pimary Prevention, Arch Intern Med, Apr. 10, 1995, pp. 701-709, vol. 155.
David M. Essayan, MD, Cyclic Nucleotide phosphodiesterases, J. Allergy Clinical Immuno, 2001, pp. 671-680, 108.
Delbeke et al., Urinary Excretion of Theobromine in Horses Given Contaminated Pelleted Food, Veterinary Research Communications, 1991, pp. 107-116, 15.
Desch et al., Effect of Cocoa Products on Blood Pressure: Systematic Review and Meta-Analysis, American Journal of Hypertension, Jan. 2010, pp. 97-103, 23-1.
Dickinson et al., Lifestyle interventions to reduce raised blood pressure: a systematic review of randomized controlled trials, Journal of Hypertension, 2006, pp. 215-233, vol. 24 No. 2.
Eeftinck et al., Nexfin Noninvasive Continuous Blood Pressure Validated Against Riva-Rocci/Korotkoff, American Journal of Hypertension, Apr. 2009, pp. 378-383, vol. 22 No. 4.
Egan et al., Does Dark Chocolate Have a Role in the Prevention and Management of Hypertension, Hypertension, 2010, pp. 1289-1295 (plus 2 extra pages for a correction to the article), 55.
Engler et al., Flavonoid-Rich Dark Chocolate Improves Endothelial Function and Increases Plasma Epicatechin Concentrations in Healthy Adults, Journal of the American College of Nutrition, 2004, pp. 197-204, vol. 23 No. 3.
Eteng et al., Recent advances in caffeine and theobromine toxicities: a review, Plant Foods for Human Nutrition, 1997, pp. 231-243, 51.

Farouque et al., Acute and chronic effects of flavanol-rich cocoa on vascular function in subjects with coronary artery disease: a randomized double-blind placebo-controlled study, Clinical Science, 2006, pp. 71-80, 111.
Fisher et al., Flavanol-rich cocoa induces nitric-oxide-dependent vasodilation in healty humans, Journal of Hypertension, 2003, pp. 2281-2286, vol. 21 No. 12.
Fornai et al., A1 and A2a receptors mediate inhibitory effects of adenosine on the motor activity of human colon, Neurogastroenterol Motil, 2009, pp. 451-466, 21.
Gisolf et al., Sublingual Nitroglycerin Used in Routine Tilt Testing Provokes a Cardiac Output-Mediated Vasovagal Response, Journal of the American College of Cardiology, 2004, pp. 588-593, vol. 44 No. 3.
Grassi et al., Cocoa Reduces Blood Pressure and Insulin Resistance and Improves Endothelium-Dependent Vasodilation in Hypertensives, Hypertension, Aug. 2005, pp. 398-405.
Grassi et al., Short-term administration of dark chocolate is followed by a significant increase in insulin sensitivity and a decrease in blood pressure in healthy persons, American Journal of Cardiology, 2005, pp. 611-614, 81-3.
Guelen et al., Validation of brachial aartery pressure reconstruction from finger arterial pressure, Journal of Hypertension, 2008, pp. 1321-1327, vol. 26 No. 7.
Hamed et al., Dark Chocolate Effect on Platelet Activity, C-Reactive Protein and Lipid Profile: A Pilot Study, Southern Medical Journal, Dec. 2008, pp. 1203-1208, vol. 101 No. 12.
Haynes et al., Helping Patients Follow Prescribed Treatment Clinical Applications, JAMA The Journal of the American Medical Association, Dec. 11, 2002, pp. 2880-2883, vol. 288 No. 22.
He et al., Effect of Cocoa Tea (*Camellia ptilophylla*) Co-Administrated with Green Tea on Ambulatory Behaviors, Bioscience, Biotechnology, and Biochemistry, 2009, pp. 957-960, vol. 73, Issue 4.
Heiss et al., Endothelial Function, Nitric Oxide, and Cocoa Flavanols, Journal of Cardiovascular Pharmacology, 2006, pp. S128-S135, vol. 47 Supp. 2.
Heiss et al., Improvement of Endothelial Function With Dietary Flavanols Is Associated With Mobilization of Circulating Angiogenic Cells in Patients With Coronary Artery Disease, Journal of the American College of Cardiology, Jul. 13, 2010, pp. 218-224, vol. 56 No. 3.
Hertog et al., Dietary antioxidant flavonoids and risk of coronary heart disease: the Zutphen Elderly Study, The Lancet, Oct. 23, 1993, pp. 1007-1011, vol. 342.
Hicks et al., Tea preapration and its iinfluence on methylxanthine concentration, Food Research International, Feb. 26, 1996, pp. 325-330, 29; 3-4, Elsevier Science Ltd.
Hodgson et al., Effects on blood pressure of drinking green and black tea, Journal of Hypertension, 1999, pp. 457-463, vol. 17 No. 4.
IPRP2 in PCTEP2009066294, dated Apr. 5, 2011, WO.
IPRP2 in PCTEP2011050574, dated Jul. 3, 2012, WO.
Iversen, Portionierbare Eiskrem, Grindsted Products, 1982, 416-418 (with English human translation), 14, DK.
Joseph H. Gans, Dietary Influences on Theobromine-Induced Toxicity in Rats, Toxicology and Applied Pharmacology, 1982, pp. 312-320, 63.
Kamphuis et al., Vascular Effects of Pentoxifylline in Humans, Journal of Cardiovascular Pharmacology, 1994, pp. 648-654, 24.
Karim et al., Effects of Cocoa Extracts on Endothelium-Dependent Relaxation, The Journal of Nutrition, 2000, pp. 2105S-2108S, 130.
Kelly, C.J., Effects of theobromine should be considred in future studies, American Journal Clin. Nutr., 2005, pp. 486-487, 82.
Knekt et al., Flavonoid intake and coronary mortality in Finland: a cohort study, BMJ, Feb. 24, 1996, pp. 478-481, vol. 312.
Laurent et al., Expert consensus document on arterial stiffness: methodological issues and clinical applications, European Heart Journal, 2006, pp. 2588-2605, 27.
Lelo et al., Comparative pharmacokinetics of caffeine and its primary demethylated metabolites paraxanthine, theobromine and theophylline in man Mentions theobromine as a cardiotonic, British Journal of Clinical Pharmacology, 1986, pp. 177, 22.

(56) References Cited

OTHER PUBLICATIONS

Mancia et al., 2007 Guidelines for the Management of Arterial Hypertension, Journal of Hypertension, 2007, pp. 1105-1187, 25.
Mathur et al., Cocoa Products Decrease Low Density Lipoprotein Oxidative Susceptibility but Do Not Affect Biomarkers of Inflammation in Humans, Journal of Nutrition, Sep. 6, 2002, pp. 3663-3667, 132.
Mellor et al., High-cocoa polyphenol-rich chocolate improves HDL cholesterol in Type 2 diabetes patients, Diabetic Medicine, 2010, pp. 1318-1321, 27.
Method for Improving the Taste Quality of Food and Beverage Containing Cacao Mass, Cocoa Cake or Cocoa Powder; and Food and Beverage Where Taste Quality is Improved, Laid-Open Gazette, Japan Patent Office, Jan. 18, 2007.
Monagas et al., Effect of cocoa powder on the modulation of inflammatory biomarkers in patients at high risk of cardiovascular disease, The American Journal of Clinical Nurition, 2009, pp. 1144-1150, 90.
Mumford et al., Absorption rate of methylxanthines following capsules, cola and chocolate, Eur J. Clin Pharmacol,, 1996, pp. 319-325, vol. 51.
Muniyappa et al., Cocoa consumption for 2 wk enhances insulin-mediated vasodilatation without improving blood pressure or insulin resistance in essential hypertension 1-3, The American Journal of Clinical Nutrition, 2008, pp. 1685-1696, 88.
Muniyappa et al., Cocoa consumption for 2 wk enhances insulin-mediated vasodilatation without improving blood pressure or insulin resistance in essential hypertension, American Journal of Clin. Nutr., 2008, pp. 1685-1696, 88.
Murphy et al., Dietary flavanols and procyanidin oligomers from cocoa (*Theobroma cacao*) inhibit platelet function, American Journal of Clin. Nutr., 2003, pp. 1466-1473, 77.
Noordzij et al., Blood pressure response to chronic intake of coffee and caffeine: a meta-analysis of randomized controlled trials, Journal of Hypertension, 2005, pp. 921-928, vol. 23 No. 5.
O'Rourke, MD et al., Differential Impact of Blood Pressure-Lowering Drugs on Central Aortic Pressure and Clinical Outcomes, Circulation, Mar. 7, 2006, pp. 1213-1225, 113.
Opposition in EP1505881 (EP03735454), Opposition in EP1505881 (EP03735454), Oct. 21, 2009.
Ostertag et al., Impact of dietary polyphenols on human platelet funciton—A critical review of controlled dietary intervention studies, Mol. Nutr. Food Res., 2010, pp. 60-81, 54.
Pauca et al., Prospective Evaluation of a Method for Estimating Ascending Aortic Pressure From the Radial Artery Pressure Waveform, Hypertension, Jul. 11, 2001, pp. 932-937, 38.
Ramirez-Sanchez et al., (−)-Epicatechin Activation of Endothelial Cell Ednothelial Nitric oxide Synthase, Nitric Oxide, and Related Signaling Pathways, Hypertension, 2010, pp. 1398-1405, vol. 55.
Rein et al., Cocoa inhibits platelet activation and function, The American Journal of Clinical Nutrition, 2000, pp. 30-35, 72.
Richelle et al., Plasma kinetics in man of epicatechin from black chocolate, European Journal of Clinical Nutrition, 1999, pp. 22-26, 53.
Roman et al., Central Pressure More Strongly Relates to Vascular Disease and Outcome Than Does Brachial Pressure. The Strong Heart Study, Hypertension, 2007, pp. 197-203, vol. 50.
Roura et al., Milk Does Not Affect the Bioavailability of Cocoa Powder Flavonoid in Healthy Human, Annals of Nutrition & Metabolism, 2007, pp. 491-498, 51.
Sanchez et al., Changes in Arterial Blood Pressure of a Soluble Cocoa Fiber Product in Spontaneously Hypertensive Rats, J. Agric. Food Chem, 2010, pp. 1493-1501, vol. 58.
Schewe et al., How do dietary flavanols improve vascular function? A position paper, Archives of Biochemistry and Biophysics, 2008, pp. 102-106, vol. 476.
Schroeter et al., (−)-Epicatechin mediates beneficial effects of flavanol-rich cocoa on vascular function in humans, PNAS, 2006, pp. 1021-1029, vol. 103, No. 4.
Search Report in EP08156161, dated Nov. 4, 2008.
Search Report in EP08172986, dated Feb. 23, 2009.
Search Report in EP08172987, dated Feb. 23, 2009, EP.
Search Report in EP08172988, dated Aug. 4, 2009, EP.
Search Report in EP09158324, dated Mar. 10, 2010, EP.
Search Report in EP09177845, dated Mar. 12, 2010.
Search Report in EP09177846, dated Mar. 2, 2010, EP.
Search Report in EP10152665, dated Mar. 4, 2010, EP.
Search Report in PCTEP2009066294, dated Jul. 30, 2010, WO.
Search Report in PCTEP2011050574, dated Apr. 29, 2011, WO.
Shiina et al., Acute effect of oral flavonoid-rich dark chocolate intake on coronary circulation, as compared with nonflavonoid white chocolate, by transthoracic Doppler echocardiography in healthy adults, International Journal of Cardiology, Jan. 2009, pp. 424-429, vol. 31 Issue 3.
Smit et al., Reinforcing effects of caffeine and theobromine as found in chocolate, Psychopharmacology, 2005, pp. 101-106.
Smulyan et al., Cuff and aortic pressure difference during dobutamine infusion: A study of the effects of systolic blood pressure amplication, American Heart Journal, 2010, pp. 399-405, vol. 159, No. 3.
Soffietti et al., Toxic Effects of Theobromine on Mature and Immature Male Rabbits, Journal of Comparative Pathology J Comp. Path., 1989, pp. 47-58, vol. 100.
Stergiopulos et al., Computer Simulation of Arterial Flow with Applications to Arterial and Aortic Stenoses, J. Biomechanics, 1992, pp. 1477-1488, vol. 25, No. 12.
Tarka et al., Effects of Continuous Administration of Dietary Theobromine on Rat Testicular Weight and Morphology, Toxicology and Applied Pharmacology, 1981, pp. 76-82, 58.
Tarka et al., Theobromine kinetics and metabolic disposition, Clinical Pharmacology & Therapeutics, 1983, pp. 546-555, vol. 34 No. 4.
Taubert et al., Effect of Cocoa and Tea Intake on Blood Pressure A Meta-analysis, Archives of Internal Medicine The Journal of the American Medical Association, 2007, pp. 626-634, 167.
Taubert et al., Effects of low habitual cocoa intake on blood pressure and bioactive nitric oxide: a randomized controlled trial, JAMA The Journal of the American Medical Association, 2007, pp. 49-60, 298.
Theobromine, IARC Summary & Evaluation, 1991, Retrieved from the internet:http://www.inchem.org/documents/iarc/vo151/06-theobromine.html pp. 1-3, vol. 51.
Umemura et al., Effects of Acute Administration of Caffeine on Vascular Function, The American Journal of Cardiology, 2006, pp. 1538-1541, 98.
Usmani et al., Theobromine inhibits sensory nerve activation and cough, The FASEB Journal,, 2005, pp. 231-233, 19.
Vasan et al., Impact of High-Normal Blood Pressure on the Risk of Cardiovascular Disease, The New England Journal of Medicine, 2001, pp. 1291-1297, vol. 345.
Vlachopoulos et al., Effect of Dark Chocolate on Arterial Function in Healthy Individuals, American Journal of Hypertension, 2005, pp. 785-791, vol. 18, No. 6.
W. Dock, The Use of Theobromine for Pain of Arteriosclerotic Origin, California and Western Medicine, 1926, pp. 636-638, 25-5.
Wang et al., Theobromine toxicity on Sertoli cells and comparison with cocoa extract in male rats, Toxicology Letters, 1994, pp. 155-164, 70.
Weber et al., Cholesteryl ester transfer protein and its inhibition, Cellular and Molecular Life Sciences, 2010, pp. 3139-3149, 67.
Westerhof et al., An artificial arterial system for pumping hearts, Journal of Applied Physiology, 1971, pp. 776-781, vol. 31 No. 5.
Westerhof et al., Analog Sturdies of the Human Systemic Arterial Tree, J. Biomechanica, 1969, pp. 121-143, 2-2.
Westerhof et al., Forward and backward waves in the Arterial System, Cardiovascular Research, 1972, pp. 648-656, 6.
Westerhof et al., Location of a reflection Site is Elusive. Consequences for the Calculation of Aortic Pulse Wave Velocity., Hypertension, 2008, pp. 478-483, 52.
Westerhof, Arterial viscoelasticity: A Generalized Model Effect on Input Impedance and Wave Travel in the Systematic Tree, Journal of Biomechanics, 1970, pp. 357-379, vol. 3.
Wilkinson et al., The influence of heart rate on augmentation index and central arterial pressure in humans, Journal of Physiology, 2000, pp. 263-270, 525-1.

(56) References Cited

OTHER PUBLICATIONS

Williams, M.D. et al., Impact of Heart Rate on Central Aortic Pressures and Hemodynamics, Journal of the American College of Cardiology, 2009, pp. 705-713, 54-8.
Witzlack et al., cAMP-induced expression of ABCA1 is associated with MAP-kinase-pathway activation, Biochemical and Biophysical Research Communications, 2007, pp. 89-94, 363.
Written Opinion in EP08156161, dated Nov. 4, 2008.
Written Opinion in EP08172986, dated Feb. 23, 2009.
Written Opinion in EP08172987, dated Feb. 23, 2009, EP.
Written Opinion in EP08172988, dated Aug. 4, 2009, EP.
Written Opinion in EP09158324, dated Mar. 10, 2010, EP.
Written Opinion in EP09177845, dated Mar. 12, 2010, EP.
Written Opinion in EP09177846, dated Mar. 2, 2010, EP.
Written Opinion in EP10152665, dated Mar. 4, 2010, EP.
Written Opinion in EP11720085, dated Apr. 13, 2015.
Written Opinion in PCTEP2009066294, dated Jul. 30, 2010, WO.
Written Opinion in PCTEP2011050574, dated Apr. 29, 2011, WO.
Zannis et al., Role of apoA-I, ABCA1, LCAT, and SR-BI in the biogenesis of HDL, Journal of Molecular Medicine, 2006, pp. 276-294, 84.
Allen et al., Daily Consumption of a Dark Chocolate Containing Flavanols and Added Sterol Esters Affects Cardiovascular Risk Factors in a Normotensive Population with Elevated Cholesterol, The Journal of Nutrition, 2008, 137, 725-731.
Baba et al., Continuous intake of polyphenolic compounds containing cocoa powder reduces LDL oxidative susceptibility and has beneficial effects on plasma HDL-cholesterol concentrations in humans, Am J Clin Nutr, 2007, 85, 709-717.
Cooper et al., Predictive Relatiionship between Polyphenol and Nonfat Cocoa Solids Content of Chocolate, J Agric Food Chem, 2008, 56, 260-265.
Crews Jr. et al., A double-blind, placebo-controlled, randomized trial of the effects of dark chocolate and cocoa on variables associated with neuropsychological functioning and cardiovascular health: clinical findings from a sample of healthy, cognitively intact older adults, Am J Clin Nutr, 2008, 87, 872-80.
De Graaf, Consumption of tall oil-derived phytosterols in a chocolate matrix significantly decreases plasma total and low-density lipoprotein-cholesterol levels, British Journal of Nutrition 2002 88 pp. 479-488.
Eteng et al, Theobromine Rich Cocoa Powder Induces Weight Loss and Changes in Lipid Profile of Obese Wistar Rats, Discovery and Innovation, Sep. 1, 2006, 191-196, vol. 18 No 3.
Eteng et al., Comparative Effects of Theobromine and Cocoa Extract on Lipid Profile in Rats, Nutrition Research 2000 vol. 20 No. 10 pp. 1513-1517.
Eteng et al., Theobromine Administratiion Inhibits Platelet Aggregation and Elevates Serum HDL-Cholesterol in Hyperlipidemic Wistar Rats, Global Journal of Pure and Applied Sciences, 2000, 89-93, 6(1).
Jalil et al., Effects of cocoa extract containing polyphenols and methylxanthines on biochemical parameters of obese-diabetic rats, J Sci Food Agric, 2009, 130-137, 89.
Kochhar, Influence of Processing on Sterols of Edible Vegetable Oils, Prog. Lipid Res.1983 vol. 22 161-168, Pergamon Press Ltd., GB.
Mensink et al., Effects of dietary fatty acids and carbohydrates on the ratio of serum total to HDL cholesterol and on serum lipids and apolipoproteins: a meta-analysis of 60 controlled trials, Am J Clin Nutr, 2003, 1146-1155, 77.
Mursu et al., Dark Chocolate Consumption Increases HDL Cholesterol Concentration and Chocolate Fatty Acids May Inhibit Lipid Peroxidation in Healthy Humans, Free Radical Biology & Medicine, 2004, 1351-1359, 37 (9), Elsevier Inc.
Polagruto et al., Cocoa Flavanol-Enriched Snack Bars Containing Phytosterols Effectively Lower Total and Low-Density Lipoprotein Cholesterol Levels, Journal of the American Dietetic Association, 2006, 1804-1813, 106.
Wan et al., Effects of cocoa powder and dark chocolate on LDL oxidative suceptibility and prostaglandin concentrations in humans, Am J Clin Nutr, 2001, 596-602, 74.
International Search Report for International Application No. PCT/EP2011/057816 with Written Opinion dated Jul. 11, 2011.
Co-pending application Drajer et al., U.S. Appl. No. 13/575,339, filed Jul. 26, 2012.

* cited by examiner

THEOBROMINE FOR INCREASING HDL-CHOLESTEROL

FIELD OF THE INVENTION

The present invention relates to a method for increasing HDL-cholesterol in humans, and/or for increasing the ratio HDL-cholesterol/LDL-cholesterol in humans, and to theobromine for use in the treatment of increasing HDL-cholesterol in humans, and/or to theobromine for use in the treatment of increasing the ratio HDL-cholesterol/LDL-cholesterol in humans, and to the use of theobromine for increasing HDL-cholesterol in humans, and/or to the use of theobromine for increasing the ratio HDL-cholesterol/LDL-cholesterol in humans.

BACKGROUND OF THE INVENTION

Since several decades it is widely known, both among physicians as well as a large part of the general (adult) public, especially in the Western world (Europe, North America) that high cholesterol (in blood) is a marker or indication for an increased risk on cardiovascular diseases. Hence, various medicaments have been developed to reduce the level of cholesterol (in blood). Since more recently, it is generally believed that not all cholesterol in this connection is "bad".

More specifically, it is the low density lipoprotein cholesterol (or even more specifically the non-high density lipoprotein cholesterol) that is preferably kept below a certain value. As it is believed that a relatively high level of high density lipoprotein cholesterol can help reducing the level and/or alleviate the negative effects of low density (or non-high density-) lipoprotein cholesterol, it is believed that it may be desired that the level of high density lipoprotein cholesterol is relatively high, or can be increased, and/or that the ratio high density lipoprotein cholesterol over low density lipoprotein cholesterol (or the ratio high density lipoprotein cholesterol over non-high density lipoprotein cholesterol) preferably kept above a certain ratio or can be increased in many humans.

High density lipoprotein cholesterol is often abbreviated to HDL-cholesterol (or herein: HDL-C) and low density lipoprotein cholesterol is often abbreviated to LDL-cholesterol (or herein: LDL-C), and non-high density lipoprotein cholesterol is often abbreviated as non-HDL-cholesterol (or herein: non-HDL-C). When referred to levels of the various forms of cholesterol, it is meant herein cholesterol in blood in humans. Such cholesterol levels are usually measured as serum (LDL-, HDL-, non-HDL-, or total-) cholesterol or plasma (LDL-, HDL-, non-HDL, or total-) cholesterol. Non-HDL-C is herein total cholesterol (TC) minus HDL-C.

Hence, it is believed that health benefits can be achieved in humans by lowering low density lipoprotein cholesterol (or LDL-cholesterol, herein abbreviated to LDL-C) and/or by increasing the level of high density lipoprotein cholesterol (or HDL-cholesterol, herein HDL-C) and/or by increasing (molar or weight) ratio HDL-C over LDL-C. There are medicaments (prescription drugs) available that are aimed for one or more of these.

Apart from such medicaments, there are also food products that are enriched in edible actives, often actives that do exist in natural sources, that can achieve or are believed to achieve a lowering of LDL-C and/or an increase of HDL-C. In this connection, since the 1960's there exist food products (e.g. spreads and margarines) that contain polyunsaturated fatty acids that help reducing cholesterol in blood (of humans). More recently, products have appeared on the market in Europe and the USA that contain plant sterols or plant stanols (or esters of these sterols or stanols) which are also believed to be able to reduce total cholesterol or LDL-C.

Still, there is a desire for (further) actives that specifically increase HDL-C, and more preferably increase the ratio HDL-C/LDL-C, and/or increase HDL-C/non-HDL-C, e.g. as such can lead to improved blood lipids (including an improved blood lipids profile). Such active could be a medicament, but, in order to help people maintain a healthy lifestyle, such does not need to be a medicament. Such a component that increases HDL-C, preferably not at the expense of increasing also LDL-C or non-HDL-C, can be consumed on its own or conveniently be combined with one or more actives which does not have an effect on HDL-C, but which is already known to reduce LDL-C or non-HDL-C.

A large range of naturally occurring components have been investigated to achieve such benefit, such as (methoxy) flavonoids. The effect of cocoa, as a rich source of flavonoids, has been studied quite extensively in this respect.

Wan et al (Am J. Clin. Nutr. 74, pp 596-602, 2001) discloses a study in which humans were fed ("long term", without indicating how long) a diet containing 22 g cocoa powder+16 g dark chocolate per daily dosage. Such diet contained 614 mg theobromine per day, which was however controlled for in the control diet (550 mg theobromine/day). They report a HDL-cholesterol increase of about 4%, and a LDL-cholesterol increase of 4.6%. Hence, the ratio HDL-C/LDL-C is not substantially changed.

De Graaf et al (British Journal of Nutrition, 88, pp 479-488, 2002) disclose chocolates enriched in plant sterols, and their study is on humans (for 4 weeks), with a dosing of 31.5 g chocolate and 1.8 g phytosterols per day. No effect is reported on HDL-C.

Mursu et al (Free Radical Biology and Medicine, 37(9), pp 1351-1359, 2004) shows that 75 g dark chocolate daily for 3 weeks can increase serum HDL-C (>11%), when compared to a placebo of white chocolate not containing polyphenols.

Baba et al (Am. J. Clin. Nutr., 85 pp 709-717, 2007) show that a daily diet containing 26 g cocoa powder for 12 weeks showed an increase of plasma HDL-C (17%) compared to the control group. LDL-C was reduced by 8% compared to the control group. The same research group reported data from a dose-response study with low (13 g), moderate (19.5 g) and high levels of cocoa powder (26 g) (J. Nutr. 137 pp 1436-1441, 2007). HDL-C increased compared to placebo by 3, 5 and 7%, respectively. The placebo was adjusted to control for theobromine content in the cocoa powders.

Crews et al (Am. J. Clin. Nutr. 87, pp 872-880, 2008) disclose that the effect of 6 week daily consumption of 37 g dark chocolate (which they say contains 60% cacao, equaling 11 g natural cocoa) plus 237 ml of a cocoa beverage also containing about 11 g natural cocoa (i.e. daily 22 g cocoa) on HDL-C or LDL-C was not statistically significant (only an increase of heart rate was noted).

M U Eteng et al (Nutrition Research, Vol. 20 No 10, pp 1513-1517, 2000), disclose that theobromine, when given to Wistar rats in an amount of 700 mg/kg body weight, decreased total cholesterol, LDL-cholesterol, and triglycerides, and elevated HDL-cholesterol in said rats.

M U Eteng et al (Discovery and Innovation, 18(3), pp 191-196, 2006) disclose that theobromine-rich cocoa powder, when given in the diet to Wistar rats in a dose of 3% to 15% cocoa powder (containing to 56-265 mg theobromine, respectively) daily in the diet for 4 weeks, lead to body weight changes and changes in the lipid profile in said rats.

M U Eteng et al (Journal of Pure and Applied Sciences, 6(1) pp 89-93, 2000) refers to trials with Wistar rats which were given 600 or 700 mg theobromine per kg body weight.

JP patent application 2006/151,878 refers to the combined use of *curcuma* or *curcuma* plant extract together with a xanthine derivative as hypoglycaemic agent for treating diabetes mellitus, and for the treatment of hyperlipedemia.

JP patent application 2001/169,753 discloses that soy protein and chitosan reduce blood cholesterol, but that one should take large dosages of such. This document aims to provide a composition that can:

suppress a rise in total cholesterol, and
suppress a reduction in HDL-C, wherein not so high dosages of soy protein or chitosan are needed. It refers that this can be achieved by a composition with 4 components together: a xanthine derivative (caffeine being preferred), a dietary fibre, an amino acid promoting glucagon secretion, and a vegetable protein.

H Yokogoshi et al, Nutritional Reports International, October 1983, volume 28, no. 4, pp 805-814, disclose that in Wistar rats, fed on a diet containing 19.4% cocoa for 2 weeks, the level of HDL-C increases when compared to a diet not containing cocoa. Serum total cholesterol of rats fed a diet supplemented with 0.3% of theobromine was significantly increased.

A M Jalil et al, J Sci Food Agric 89, pp 130-137 (2009) disclose that intake of a cocoa extract supplemented with polyphenols and methylxanthines in obese-diabetic rats, significantly reduced plasma total cholesterol, triglycerides, and LDL-C, but did not result in a significant difference in HDL-C.

R R Allen et al, J. Nutr. 137, pp 725-731 (2008) disclose that consumption per day of 2 cocoa-flavonol containing dark chocolate bars, enriched in 1.1 g sterol esters per bar, in humans with elevated serum cholesterol, reduces blood cholesterol levels.

J A Polagruto et al, Journal of the American Dietetic Association, vol. 206, no. 11, pp 1804-1813 (2006) disclose that a consumption by humans of cocoa flavanol-enriched snack bars containing phytosterols effectively lowers total cholesterol and LDL-C, and that it does not affect HDL-C levels.

SUMMARY OF THE INVENTION

Hence, there is a desire for an active, preferably naturally occurring, which, when ingested regularly (preferably daily, or at least 5 times a week), and preferably at least for some time (preferably at least for 2 weeks, more preferably at least for 3 weeks, more preferably longer), can help in increasing HDL-C in humans. Preferably, such is achieved whilst the concentration of LDL-C and/or non-HDL-C is not increased, at least not by more than 5%, preferably not by more than 3%. The amount of HDL-C increase is preferably at least 5%, more preferably at least 8%, even more preferably at least 10%, when compared to a placebo (all increases and decreases herein in a statistically significant amount). There is also a desire for an active that, when ingested regularly (preferably daily, or at least 5 times a week), and preferably at least for some time (preferably at least for 2, more preferably at least for 3 weeks, more preferably longer), can help in increasing the ratio HDL-C/LDL-C in humans and/or that can help in increasing the ratio HDL-C/non-HDL-C in humans. Preferably such increase is at least 5%, more preferably at least 8%, even more preferably at least 10%, when compared to a placebo (preferably in a statistically significant amount). There is also a desire for a method or use of such active for increasing HDL-C and/or increasing the ratio HDL-C/LDL-C and/or increasing the ratio of HDL-C/non-HDL-C. Such raise of HDL-C in combination with lower increase of LDL-C and/or improved ratio of HDL-C/LDL-C is believed to improve the blood lipids (or in other words improve the blood lipids profile), which are both desirable objectives. Preferably, the effects on HDL-C, the ratio HDL-C/LDL-C, and/or the ratio HDL-C/non-HDL-C as set out above are achieved without significantly raising peripheral blood pressure. Preferably, the effects on HDL-C, the ratio HDL-C/LDL-C, and/or the ratio HDL-C/non-HDL-C as set out above are achieved without significantly raising the level of triglyceride in blood or serum, as such is considered undesired. There is also a desire for suitable edible compositions, preferably in the format of food products, that comprise such active. Preferred food formats in this context are emulsions such as e.g. spreads like butter alternative.

The active desired is preferably to be consumed regularly, and is preferably also not seen as a medicament. Hence, there is a desire for food products containing the desired active that fit in many diets, and preferably such food product should be such that consumers usually consume an amount which is fairly constant and predictable, so as to limit the chance of over- and under-dosing (over and below the daily amount for a good and safe effect). Also, such food products are preferably such that they are already seen as carriers for cardiovascular benefits, and preferably blood lipid-regulating food products. Typical examples of this in the diets in Europe and North America are spreads (margarine, for e.g. spreading on bread), and beverages, especially minidrinks (typically "shots" of a volume of e.g. between 50 and 150 ml or even between 50 and 125 ml, which are frequently offered as carrier for ingredients with a real or perceived health benefit, such as to provide pro- or prebiotics, for regulating LDL-cholesterol, for regulating blood pressure) and dairy-like products (i.e. fermented) as drinkable yoghurt-like products (the same or similar sort of uses).

It has now surprisingly been found that such objectives may be achieved, at least in part, by the ingestion of theobromine. It was found that by the ingestion of theobromine, HDL-C (as measured in serum or plasma) in humans can be increased (raised) by at least 5%. It was also found that such can be achieved in the absence of a rise in LDL-C or non-HDL-C (in serum or plasma), or at least by a rise in LDL-C or non-HDL-C (in serum or plasma, or blood) in humans by less than 5%. This is beneficial for the ratio HDL-C/LDL-C or HDL-C/non-HDL-C in humans (in serum or plasma, or in blood), or in other words for improving blood lipids, or the blood lipids profile.

Hence, in a first aspect the present invention relates to theobromine for use in the treatment of improving blood lipids (including improving blood lipids profile).

In a second aspect the present invention relates to theobromine for use in the treatment of increasing HDL-cholesterol in humans.

In a third aspect, the present invention relates to theobromine for use in the treatment of increasing the ratio HDL-cholesterol/LDL-cholesterol in humans.

In a fourth aspect the present invention relates to theobromine for use in the treatment of increasing the ratio HDL-cholesterol/non-HDL-cholesterol in humans.

More specifically, in the above four aspects said treatment involves ingestion of theobromine by humans. Hence, the invention relates to theobromine for use in the treatment of improving blood lipids (including blood lipids profile) and/or increasing HDL-C in humans by ingestion of theobromine by humans, and/or to theobromine for use in the treatment of increasing the ratio HDL-C/LDL-C in humans by ingestion of theobromine by humans, and/or to theobromine for use in the treatment of increasing the ratio HDL-C/non-HDL-C in humans by ingestion of theobromine by humans.

In a further aspect, the present invention relates to theobromine for use in the treatment of increasing the ratio HDL-cholesterol/LDL-cholesterol in humans.

In a further aspect the present invention relates to theobromine for use in the treatment of increasing the ratio HDL-cholesterol/non-HDL-cholesterol in humans.

The invention further relates to a method for improving blood lipids and/or blood lipids profile by ingestion of theobromine. More specifically, the invention further relates to a method for improving blood lipids and/or blood lipids profile for a person in need of the treatment of improving blood lipids and/or blood lipids profile, by ingestion of theobromine. The invention further relates to a method for increasing HDL-cholesterol in a human, which method comprises administering to the human an HDL cholesterol raising effective amount of theobromine. The invention further relates to a method for increasing HDL-cholesterol in humans comprising ingestion of an HDL cholesterol raising effective amount of theobromine. More specifically, the invention further relates to a method for increasing HDL-cholesterol in humans, for a person in need of treatment of increasing HDL-cholesterol, by ingestion of an HDL-cholesterol raising effective amount of theobromine.

The invention also relates to a method for increasing the ratio HDL-cholesterol/LDL-cholesterol in humans by ingestion of theobromine. More specifically, the invention further relates to a method for increasing the ratio HDL-cholesterol/LDL-cholesterol in a human, which method comprises administering to the human an HDL-cholesterol/LDL-cholesterol ratio raising effective amount of theobromine. The invention also relates to a method for increasing the ratio HDL-cholesterol/non-HDL-cholesterol in humans by ingestion of theobromine. More specifically, the invention further relates to a method for increasing the ratio HDL-cholesterol/non-HDL-cholesterol in a human, which method comprises administering to the human an HDL-cholesterol/non-HDL-cholesterol ratio raising effective amount of theobromine.

In these methods, the effective amount is from 300 to 2000 mg theobromine per day, preferably from 400 to 1800 mg theobromine per day, more preferably from 600 to 1400 mg of theobromine per day, even more preferably from 700 to 1300 mg theobromine per day, most preferably from 750 to 1250 mg theobromine per day. These amounts per day in these methods are daily dosages. Preferably, in these methods this is achieved by administering to the human a foodstuff (including beverages) comprising at least 0.1% by weight of theobromine on the total composition, preferably at least 0.2%, more preferably at least 0.5% by weight of theobromine on the composition. Preferred embodiments of foodstuffs that can be used for such are set out in the detailed description of the invention, hereafter. The theobromine in these methods (and the compositions in such methods) may be from cocoa, but does not need to be. Cocoa contains next to e.g. theobromine also polyphenols. E.g. for colour reasons, it is preferred that the levels of polyphenols (e.g. from cocoa) ingested in these methods and present in the compositions for use in these methods are not more than 5 times the amount of theobromine ingested in these methods and present in such compositions, or in other words: the amount of polyphenols (e.g. from cocoa) ingested in the methods and present in the compositions for use in these methods referred to herein is preferably between 0% and 500% on the weight of theobromine ingested or present in the compositions, more preferably from 0% to 200% on the weight of theobromine ingested or present in the compositions, even more preferably from 0% to 50% on the weight of theobromine ingested or present in the compositions. Epicatechin is a polyphenol present in substantial amounts in cocoa, and e.g. for reasons of taste (e.g. undesired bitterness) it is preferred if the amount of epicatechin ingested in these methods and present in the compositions for use in these methods is not more than the amount of theobromine ingested in these methods and present in the compositions for use in these methods, or in other words: the amount of epicatechin (e.g. from cocoa) ingested in the methods and present in the compositions for use in these methods referred to herein is preferably between 0% and 100% on the weight of theobromine ingested or present in the compositions, more preferably from 0% to 50% on the weight of theobromine ingested or present in the compositions, even more preferably from 0% to 20% on the weight of theobromine ingested or present in the compositions.

In the methods as set out herein, the increase in HDL-cholesterol in humans (in blood and/or serum) that can be achieved (when comparing humans not following the method of the present invention with humans following the present invention for at least 2 weeks) is preferably at least 5%, preferably at least 8%, more preferably at least 10%, e.g. depending on the daily dosing of theobromine. Likewise, the increase in the ratio HDL-cholesterol/LDL-cholesterol in humans (in blood and/or serum) that can be achieved is preferably at least 5%, preferably at least 8%, more preferably at least 10%, e.g. depending on the daily dosing of theobromine.

The invention also relates to edible compositions comprising theobromine and plant sterols, edible compositions comprising theobromine and PUFA's (polyunsaturated fatty acids), edible compositions comprising theobromine and statins.

DETAILED DESCRIPTION OF THE INVENTION

Cocoa and chocolate have frequently been studied for its cardiovascular effects, e.g. on blood lipid composition. However, if effects were found on blood lipids, they were so far generally attributed to one or more of the polyphenols that are present in cocoa or chocolate. Hence, for that reason usually dark chocolate is taken for such studies, as such is richer in cocoa polyphenols than milk chocolate or white chocolate. The present inventor has found such is not the case, at least not to a large extent.

"Theobromine" herein relates to the molecular structure as set out below, and is chemically known as 2,6-dihydroxy-3,7-dimethylpurine or 3,7-dimethylxanthine (chemical formula: $C_7H_8N_4O_2$, $M_w$=180.16), including the edible salts thereof.

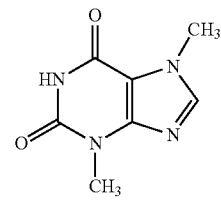

In the present invention, when referring to cholesterol (HDL-C, LDL-C, non-HDL-C, or TC) in humans, such is herein to be understood as to encompass levels of cholesterol (HDL-C, LDL-C, non-HDL-C or TC) in blood in humans. Such is generally measured as HDL-C, LDL-C, non-HDL-C and TC levels in serum and/or plasma, but for ease of reference such are herein all encompassed when referring to (levels of) HDL-cholesterol, (levels of) LDL-cholesterol, level of non-HDL-cholesterol and level of total cholesterol.

Herein, "HDL-C" is to be understood to mean high density lipoprotein cholesterol.

Herein, "LDL-C" is to be understood to mean low density lipoprotein cholesterol.

Herein, "TC" is to be understood to mean total cholesterol.

Herein, "non-HDL-C" is to be understood to mean non-high density lipoprotein cholesterol, and that such is equal to TC minus HDL-C.

Herein, the ratio HDL-C/LDL-C is to be understood to mean ratio of HDL-C to LDL-C as set out by Mensink, R. P., Zock, P. L., Kester, A. D. M. & Katan, M. B. (2003) in: Effects of dietary fatty acids and carbohydrates on the ratio of serum total to HDL cholesterol and on serum lipids and apolipoproteins: a meta-analysis of 60 controlled trials. Am J Clin Nutr 77: 1146-1155, and likewise for the ratio HDL-C/non-HDL-C.

Herein, "plant sterols" (including its singular "plant sterol") mean components which can be classified in three groups: 4-desmethylsterols, 4-monomethylsterols and 4,4'-dimethylsterols. In oils and more specifically vegetable oils they mainly exist as free sterols and sterol esters of fatty acids although sterol glucosides and acylated sterol glucosides are also present. Rice bran oil contains mainly 4,4'-dimethylsterols such as cycloartenol and 24-methylene cycloartenol, which commonly are in the form of ferulic acid esters. These 4,4'-dimethylsterol ferulic acid esters are also called oryzanol. Amongst the 4-desmethylsterols three are major plant sterols namely beta-sitosterol, stigmasterol and campesterol. There are three major plantsterols namely beta-sitosterol, stigmasterol and campesterol. Schematic drawings of the components meant are as given in "Influence of Processing on Sterols of Edible Vegetable Oils", S. P. Kochhar; Prog. Lipid Res. 22: pp. 161-188. The respective 5 alpha-saturated derivatives such as sitostanol, campestanol and ergostanol and their derivatives are also encompassed in the term plant sterol. Hence, "plant sterols" and "plant sterol" herein encompass plant sterols, esters of plant sterols, plant stanols, and esters of plant stanols and the specific compounds referred to herein. Unless specified otherwise, any specific amount of plant sterol, e.g. gram, weight ratio or weight %, is to be understood to be on the basis of free plant sterol equivalent.

Preferably the plant sterol herein is selected from the group comprising β-sitosterol, β-sitostanol, campesterol, campestanol, stigmasterol, brassicasterol, brassicastanol or a mixture thereof. Suitable sources of plant sterols are for example derived from soy bean oil, tall oil, rapeseed oil, rice bran oil or combinations of these oils.

Herein, "increase in HDL-C" is in a statistically significant amount. Herein, "increase in the ratio HDL-C/LDL-C" and "increase in the ratio HDL-C/non-HDL-C" is preferably in a statistically significant amount.

Herein, the term "polyphenols" means organic chemicals characterised by the presence of multiples of phenolic groups. Polyphenols can be found in certain plant material. It encompasses anthocyans, flavonoids, flavanols, and flavonols. Specific examples of polyphenols herein are: catechin, epicatechin, gallocatechin, epigallocatechin, epicatechin gallate, epigallocatechin gallate, quercetin, rutin, hesperidin, naringin, naringenin, genistein, and dimers, trimers, tetramers and oligomers thereof. Herein, the amount of polyphenols in a composition, when not specified otherwise e.g. by a supplier, existing analytical data or otherwise, is the amount as can be measured in such composition according to the Folin-Ciocalteu method and reported in epicatechin equivalents per gram of composition. An example of this for chocolate is set out by K A Cooper et al, J. Agric. Food Chem. 2008, 56, 260-265. The amount of epicatechin in a composition, when not specified otherwise e.g. by a supplier, existing analytical data or otherwise, can be quantified e.g. by a method as reported by K A Cooper et al, J. Agric. Food Chem. 2008, 56, 260-265.

Herein, "non-fat cocoa solids" (or NFCS) is to be understood as set out by K A Cooper et al, J. Agric. Food Chem. 2008, 56, 260-265.

Herein, "statin" (and "statins") is to be understood as a HMG-CoA reductase inhibitor, and as such encompasses the group of: atorvastatin, fluvastatin, lovastatin, pitavastatin, pravastatin, rosuvastatin, simvastatin, cerivastatin, mevastatin, and mixtures thereof. "Statin" and "statins" are herein both used interchangeably, as names, and refer to both the singular and plural, i.e. a single statin as well as mixtures (that is: a composition comprising "statins" also refers to compositions comprising only one specific statin as identified herein, next to other non-statin components).

Unless defined otherwise, any percentage or ratio of components is to be understood herein as percentage by weight, and weight ratio.

It is preferred, for reasons of e.g. efficacy and/or safety, that in the methods and for the theobromine for use in the treatment of increasing HDL-C in humans as set out herein and/or for the theobromine for use in the treatment of increasing the ratio HDL-C/LDL-C in humans as set out herein and/or for the theobromine for use in the treatment of increasing the ratio HDL-C/non-HDL-C in humans as set out herein, that such treatment or method comprises ingestion by a human of from 300 to 2000 mg theobromine per day. Such amount can be consumed all at once at a single point in the day, but also partial dosing can be done, e.g. 3 times 150 mg per day adds up to a daily dosing of 450 mg.

For reasons of e.g. balancing efficacy and safety, it may also be preferred that in the methods and for the theobromine for use in the treatments as set out herein, that such treatments or methods comprises ingestion from 400 to 1800 mg theobromine per day, preferably from 500 to 1500 theobromine mg per day, more preferably from 600 to 1400 mg theobromine per day, even more preferably from 700 to 1300 mg theobromine per day, most preferably from 750 to 1250 mg theobromine per day.

It is believed that the effects described herein are best achieved if theobromine is taken regularly and preferably also for some time. Hence, it is preferred for the theobromine for use in the treatments as set out herein that such theobromine is ingested for at least 5 days per week for at least 3 weeks, preferably for at least 5 days per week for at least 4 weeks.

Theobromine, though naturally occurring in e.g. cocoa, is also available from synthetic origin. Both are believed to be active in this connection. Synthetic theobromine is a white crystalline powder. The taste of theobromine is very bitter. For this reason, it is preferred that in the methods and for the theobromine for use in the treatments as set out herein that such theobromine is ingested in the form of encapsulates (e.g. microcapsules which can be included in food products) or bound to components (e.g. tannins) so that the bitter taste of theobromine is suppressed.

Although the use as set out herein is not believed to be the treatment of a disease (but helps people to maintain a healthy life style without the need to take prescription drugs), the invention further relates to the use of theobromine for the manufacture of a medicament or foodstuff for increasing HDL-C in humans. Likewise, the invention also relates to the use of theobromine for the manufacture of a medicament or foodstuff for increasing the ratio HDL-C:LDL-C and/or the ratio HDL-C:non-HDL-C in humans. The preferred embodiments as set out above (e.g. on amounts and dosing) are also applicable to these uses for the manufacture of a medicament or foodstuff as specified in this paragraph.

The invention further relates to the use of theobromine for increasing HDL-C in humans and/or to the use of theobromine for increasing the ratio HDL-C/LDL-C in humans and/or to the use of theobromine for increasing the ratio HDL-C/non-HDL-C in humans.

The invention further relates to compositions containing theobromine. As theobromine can be used to increase HDL-C in humans selectively (i.e. without the effect of increasing also the LDL-C or non-HDL-C, which would be undesired), it is believed that theobromine can be easily combined with known agents that (selectively or not) lower LDL-C or non-HDL-C in humans, be it prescription drugs (such as statins) or actives that are not prescription drugs but are suitable (within limits) to be included in foodstuffs (e.g. plant sterols or plant stanols or esters of such sterols or stanols). Regarding the latter, the daily dosing of such sterols or stanols is usually (for the benefit of cholesterol lowering) between 1 and 3 grams (e.g. on free plant sterol equivalent dosing). Hence, the invention further relates to an edible composition comprising theobromine and plant sterols or plant stanols or esters of plant sterols or plant stanols, wherein the amount of theobromine is between 300 and 2000, preferably between 500 and 2000 mg per daily dosing (preferably the amount of theobromine is between 400 and 1800 mg per daily dosing, more preferably from 500 to 1500 theobromine mg per daily dosing, even more preferably from 600 to 1400 mg theobromine per daily dosing, even more preferably from 700 to 1300 mg theobromine per daily dosing, most preferably from 750 to 1250 mg theobromine per daily dosing) and the amount of plant sterols or plant stanols or esters of plant sterols or plant stanols is 1 to 3 g per daily dosing (dosing preferably on free plant sterol equivalent). Other combinations of amounts of theobromine and plant sterols or plant stanols or esters of plant sterols or plant stanols may be used for some purposes, e.g. depending on price and desired effects. For this reason, it may be preferred that such edible composition comprises theobromine and plant sterols or plant stanols or esters of plant sterols or plant stanols, wherein the amount of theobromine is between 300 and 2000 mg per daily dosing (preferably wherein the amount of theobromine is between 400 and 1800 mg per daily dosing, more preferably from 500 to 1500 theobromine mg per daily dosing, even more preferably from 600 to 1400 mg theobromine per daily dosing, even more preferably from 700 to 1300 mg theobromine per daily dosing, most preferably from 750 to 1250 mg theobromine per daily dosing) and the amount of plant sterols or plant stanols or esters of plant sterols or plant stanols is more than 1.8 g per daily dosing, preferably from 2 to 3 g per daily dosing (dosing preferably on free plant sterol equivalent). It may also be preferred for e.g. reasons of efficacy, safety and or cost for an edible composition comprising theobromine and one or more from the group of plant sterols or plant stanols or esters of plant sterols or plant stanols, wherein the weight ratio theobromine:the group of plant sterols, plant sterols, esters of plant sterols or plant stanols taken together is from 0.3:1 to 1:1 (dosing plant sterols preferably on free plant sterol equivalent). For e.g. achieving the desired effect by ingestion by a human of a moderate amount of such composition, it is preferred that in such compositions, the amount of theobromine is at least 0.1% by weight of theobromine on the total composition, preferably at least 0.2% by weight of theobromine on the total composition, more preferably at least 0.5% by weight of theobromine on the total composition. The theobromine in these compositions may be from cocoa, but does not need to be. Cocoa contains next to e.g. theobromine also polyphenols. E.g. for colour reasons it is preferred that the levels of polyphenols (e.g. from cocoa) in these compositions is not more than 5 times the amount of theobromine in these compositions, or in other words: the amount of polyphenols (e.g. from cocoa) in the compositions referred to herein are preferably between 0% and 500% on the weight of theobromine in the composition, more preferably from 0% to 200% on the weight of theobromine in the composition, even more preferably from 0% to 50% on the weight of theobromine in the composition. Epicatechin is a polyphenol present in substantial amounts in cocoa, and e.g. for reasons of taste (e.g. undesired bitterness) it is preferred that the amount of epicatechin (e.g. from cocoa) present in these compositions is not more than the amount of theobromine present in these compositions, or in other words: the amount of epicatechin (e.g. from cocoa) in the compositions referred to herein is preferably between 0% and 100% on the weight of theobromine in such compositions, more preferably from 0% to 50% on the weight of theobromine in such compositions, even more preferably from 0% to 20% on the weight of theobromine in such compositions.

As an alternative to or in addition to sterols or stanols, theobromine may be combined with another agent known to have beneficial effects on blood cholesterol levels such as polyunsaturated fatty acids (including esters thereof) like EPA (eicosapentaenoic acid) and DHA (docosahexaenoic acid). In order to contribute to cardiovascular health, the combined EPA and DHA intakes of adolescents (aged 10-18) and adults (aged 19>) should be 500 mg/day. When balancing cost, safety and efficacy, compositions that comprise theobromine and EPA and/or DHA comprise such components in a weight ratio of from 1:4 to 1:0.3, more preferably from 1:3 to 1:0.5, most preferably from 1:2 to 1:0.5 (for theobromine:EPA+DHA combined). For e.g. achieving the desired effect by ingestion by a human of a moderate amount of such composition, it is preferred that in such compositions, the amount of theobromine is at least 0.1% by weight of theobromine on the total composition, preferably at least 0.2% by weight of theobromine on the total composition, more preferably at least 0.5% by weight of theobromine on the total composition. The theobromine in these compositions may be from cocoa, but does not need to be. Cocoa contains next to e.g. theobromine also polyphenols. E.g. for colour reasons it is preferred that the levels of polyphenols (e.g. from cocoa) in these compositions is not more than 5 times the amount of theobromine in these compositions, or in other words: the amount of polyphenols (e.g. from cocoa) in the compositions referred to herein are preferably between 0% and 500% on the weight of theobromine in the composition, more preferably from 0% to 200% on the weight of theobromine in the composition, even more preferably from 0% to 50% on the weight of theobromine in the composition. Epicatechin is a polyphenol present in substantial amounts in cocoa, and e.g. for reasons of taste (e.g. undesired bitterness) it is preferred that the amount of epicatechin (e.g. from cocoa) present in these compositions is not more than the amount of theobromine present in these compositions, or in other words: the amount of epicatechin (e.g. from cocoa) in the compositions referred to herein is preferably between 0% and 100% on the weight of theobromine in such compositions, more preferably from 0% to 50% on the weight of theobromine in such compositions, even more preferably from 0% to 20% on the weight of theobromine in such compositions.

As mentioned, theobromine may also be combined with prescription drugs for influencing blood cholesterol levels. For this reason, it may be preferred to combine theobromine with widely used actives like statins, e.g. to boost overall health effect and/or to be able to use lower dosings of actives like statins. For this reason, the invention further relates to an edible composition comprising theobromine (preferably in an amount of 300-2000 mg per day) and a statin (preferably 10-80 mg per day). When balancing safety and efficacy, compositions that comprise theobromine and a statin comprise such components in a weight ratio of from 200:1 to 5:1, more preferably from 100:1 to 10:1, most preferably from 50:1 to 20:1 (for theobromine:statin). The statin herein can be one or more of: atorvastatin, fluvastatin, lovastatin, pitavastatin, pravastatin, rosuvastatin, simvastatin, cerivastatin, mevastatin, and mixtures thereof. For e.g. achieving the desired effect by ingestion by a human of a moderate amount of such composition, it is preferred that in such compositions, the amount of theobromine is at least 0.1% by weight of theobromine on the total composition, preferably at least 0.2% by weight of theobromine on the total composition, more preferably at least 0.5% by weight of theobromine on the total composition. The theobromine in these compositions may be from cocoa, but does not need to be. Cocoa contains next to e.g. theobromine also polyphenols. E.g. for colour reasons it is preferred that the levels of polyphenols (e.g. from cocoa) in these compositions is not more than 5 times the amount of theobromine in these compositions, or in other words: the amount of polyphenols (e.g. from cocoa) in the compositions referred to herein are preferably between 0% and 500% on the weight of theobromine in the composition, more preferably from 0% to 200% on the weight of theobromine in the composition, even more preferably from 0% to 50% on the weight of theobromine in the composition. Epicatechin is a polyphenol present in substantial amounts in cocoa, and e.g. for reasons of taste (e.g. undesired bitterness) it is preferred that the amount of epicatechin (e.g. from cocoa) present in these compositions is not more than the amount of theobromine present in these compositions, or in other words: the amount of epicatechin (e.g. from cocoa) in the compositions referred to herein is preferably between 0% and 100% on the weight of theobromine in such compositions, more preferably from 0% to 50% on the weight of theobromine in such compositions, even more preferably from 0% to 20% on the weight of theobromine in such compositions.

The theobromine in the present case may be included in known food formats, such as e.g. spreads (butter alternatives aimed for e.g. spreading on bread). "Spread" is herein to be understood as an oil and water containing emulsion (W/O, O/W, or W/O/W), comprising 20-85% by weight of oil (oil is herein defined as including fat) and 15 to 80% water. Preferably, the spread herein has a pH of 4.8-6 (as measured by melting the spread, separating the molten fat phase and water phase, and measuring the pH of the water phase).

Preferably (for good product properties), the spread herein is a W/O type emulsion. Preferably (for good product properties, e.g. spreadability), the spread herein has a Stevens value (when measured as set out below) of between 100 and 500 gram at 15 degrees Celsius. Stevens values give an indication about the hardness (also called firmness) of a product. The Stevens value herein is determined as follows: the product is stored for 24 h at 15 degrees Celsius before measurements are done. The hardness of the product is measured with a Stevens penetrometer (Brookfield LFRA Texture Analyser (LFRA 1500), ex Brookfield EnLabs, UK) equipped with a stainless steel probe with a diameter of 6.35 mm and operated in "normal" mode. The probe is pushed into the product at a speed of 2 mm/s, a trigger force of 5 gram from a distance of 10 mm. The force required is read from the digital display and is expressed in grams.

Hence, the invention further relates to an edible emulsion (typically the spread as set out above) comprising (by weight) 20 to 85% of oil (preferably from 35% to 50%), water (preferably 15 to 80%, more preferably 50% to 65%), 0.5 to 10% theobromine (preferably from 0.8 to 5%). Preferably, such emulsion has a pH (the water phase) of 4.8-6. Preferably such emulsion is a W/0 emulsion. Preferably the emulsion has a Stevens value as set out above. Preferably, said emulsion further comprises (by weight on the emulsion) 2-20% (preferably 3-15%) of plant sterols (dosing preferably on free plant sterol equivalent). The theobromine in these spreads may be from cocoa, but does not need to be. Cocoa contains next to e.g. theobromine also polyphenols. E.g. for colour reasons it is preferred that the levels of polyphenols (e.g. from cocoa) in these spreads is not more than 5 times the amount of theobromine in these spreads, or in other words: the amount of polyphenols (e.g. from cocoa) in the spreads referred to herein are preferably between 0% and 500% on the weight of theobromine in such spreads, more preferably from 0% to 200% on the weight of theobromine in such spreads, even more preferably from 0% to 50% on the weight of theobromine in the such spreads. Epicatechin is a polyphenol present in substantial amounts in cocoa, and e.g. for reasons of taste (e.g. undesired bitterness) it is preferred that the amount of epicatechin (e.g. from cocoa) present in these spreads is not more than the amount of theobromine present in these spreads, or in other words: the amount of epicatechin (e.g. from cocoa) in the spreads referred to herein is preferably between 0% and 100% on the weight of theobromine in such spreads, more preferably from 0% to 50% on the weight of theobromine in such spreads, even more preferably from 0% to 20% on the weight of theobromine in such spreads.

Spreads herein may comprise other ingredients commonly used for spreads, such as flavouring ingredients, thickeners, gelation agents, colouring agents, vitamins, emulsifiers, pH regulators, stabilizers etc. Common amounts of such ingredients as well as suitable ways to prepare margarines or spreads are well-known to the skilled person.

The invention further relates to an edible emulsion (including spreads) as set out above, for use in the treatment of increasing HDL-cholesterol in humans and/or for use in the treatment of increasing the ratio HDL-cholesterol/LDL-cholesterol in humans, and/or for use in the treatment of increasing the ratio HDL-cholesterol/non-HDL-cholesterol in humans. For these emulsions in the use specified, it is preferred that the treatment comprises ingestion by a human of from 300 to 2000 mg theobromine per day. Likewise, for these emulsions in the use specified, it is preferred that the treatment comprises ingestion from 400 to 1800 mg theobromine per day, preferably from 500 to 1500 theobromine mg per day, more preferably from 600 to 1400 mg theobromine per day, even more preferably from 700 to 1300 mg theobromine per day, most preferably from 750 to 1250 mg theobromine per day. Also, these emulsions in the use specified, it is preferred that in the treatment mentioned herein, e.g. as mentioned above, theobromine is ingested for at least 5 days per week for at least 3 weeks, preferably for at least 5 days per week for at least 4 weeks. The theobromine in these emulsions (including spreads) may be from cocoa, but does not need to be. Cocoa contains next to e.g. theobromine also polyphenols. E.g. for colour reasons it is preferred that the levels of polyphenols (e.g. from cocoa) is not more than 5 times the amount of theobromine in these emulsions (including spreads), or in other words: the amount of polyphenols (e.g. from cocoa) in such emulsions (including spreads) referred to herein are preferably between 0% and 500% on the weight of theobromine present in the emulsions (including spreads), more preferably from 0% to 200% on the weight of theobromine present in the emulsions (including spreads, even more preferably from 0% to 50% on the weight of theobromine present in the emulsions (including spreads). Epicatechin is a polyphenol present in substantial amounts in cocoa, and e.g. for reasons of taste (e.g. undesired bitterness) it is preferred that the amount of epicatechin (e.g. from cocoa) present in these emulsions (including spreads) is not more than the amount of theobromine present in these emulsions (including spreads), or in other words: the amount of epicatechin (e.g. from cocoa) in the emulsions (including spreads) referred to herein is preferably between 0% and 100% on the weight of theobromine in such emulsions (including spreads), more preferably from 0% to 50% on the weight of theobromine, even more preferably from 0% to 20% on the weight of theobromine in such emulsions (including spreads).

As an alternative to e.g. spreads, theobromine may also be included in other food products, such as e.g. beverages, including mini-drinks ("shots", of e.g. 50-150 ml, preferably 50-125 ml, more preferably 60-120 ml packaged unit dose volume). Preferably, in such beverages, the theobromine, which raises HDL-C, is combined with an active that can lower LDL-C. Hence, the present invention further relates to a liquid composition comprising water in an amount of more than 70% by weight on the total composition (preferably more than 80% by weight based on the total composition) and less than 99.8% by weight on the total composition, theobromine in an amount of from 0.3% by weight on the total composition to 2% by weight on the total composition, plant sterols in an amount such that theobromine and plant sterols are present in a weight ratio theobromine:plant sterols of from 1:1 to 1:10 (preferably from 1:2 to 1:5) (dosing preferably on free plant sterol equivalent). The theobromine in these liquid compositions may be from cocoa, but does not need to be. Cocoa contains next to e.g. theobromine also polyphenols. E.g. for colour reasons it is preferred that the levels of polyphenols (e.g. from cocoa) in these liquid compositions is not more than 5 times the amount of theobromine in these liquid compositions, or in other words: the amount of polyphenols (e.g. from cocoa) in the liquid compositions referred to herein are preferably between 0% and 500% on the weight of theobromine in the liquid composition, more preferably from 0% to 200% on the weight of theobromine in the liquid composition, even more preferably from 0% to 50% on the weight of theobromine in the liquid composition. Epicatechin is a polyphenol present in substantial amounts in cocoa, and e.g. for reasons of taste (e.g. undesired bitterness) it is preferred that the amount of epicatechin (e.g. from cocoa) present in these liquid compositions is not more than the amount of theobromine present in these liquid compositions, or in other words: the amount of epicatechin (e.g. from cocoa) in the liquid compositions referred to herein is preferably between 0% and 100% on the weight of theobromine in such liquid compositions, more preferably from 0% to 50% on the weight of theobromine in such liquid compositions, even more preferably from 0% to 20% on the weight of theobromine in such liquid compositions.

In the liquid composition as set out above, it is preferred that the composition comprises from 85 to 99% by weight on the total composition of water. In the liquid composition as set out above, for reasons of efficacy, safety, and product formulation, it is preferred that such composition comprises theobromine in an amount of 0.4 to 1.5% by weight on the total composition.

The invention further relates to a liquid composition as set out above, for use in the treatment of increasing HDL-cholesterol in humans and/or for use in the treatment of increasing the ratio HDL-cholesterol/LDL-cholesterol in humans, and/or for use in the treatment of increasing the ratio HDL-cholesterol/non-HDL-cholesterol in humans. For these liquids in the use specified, it is preferred that the treatment comprises ingestion by a human of from 300 to 2000 mg theobromine per day. Likewise, for these liquids in the use specified, it is preferred that the treatment comprises ingestion from 400 to 1800 mg theobromine per day, preferably from 500 to 1500 theobromine mg per day, more preferably from 600 to 1400 mg theobromine per day, even more preferably from 700 to 1300 mg theobromine per day, most preferably from 750 to 1250 mg theobromine per day. Also, for these liquids in the use specified, it is preferred that in the treatment, theobromine is ingested for at least 5 days per week for at least 3 weeks, preferably for at least 5 days per week for at least 4 weeks. The theobromine in this may be from cocoa, but does not need to be. Cocoa contains next to e.g. theobromine also polyphenols. E.g. for colour reasons it is preferred that the levels of polyphenols (e.g. from cocoa) in these liquid composition for the use as specified herein are not more than 5 times the amount of theobromine in said liquid compositions, or in other words: the amount of polyphenols (e.g. from cocoa) in said liquid compositions referred to herein are preferably between 0% and 500% on the weight of theobromine in said composition, more preferably from 0% to 200% on the weight of theobromine in said composition, even more preferably from 0% to 50% on the weight of theobromine in said composition. Epicatechin is a polyphenol present in substantial amounts in cocoa, and e.g. for reasons of taste (e.g. undesired bitterness) it is preferred that the amount of epicatechin (e.g. from cocoa) present in these liquid compositions in the use as specified is not more than the amount of theobromine present in these compositions, or in other words: the amount of epicatechin (e.g. from cocoa) in said compositions referred to herein is preferably between 0% and 100% on the weight of theobromine in said compositions, more preferably from 0% to 50% on the weight of theobromine in said compositions, even more preferably from 0% to 20% on the weight of theobromine in said compositions.

Another preferred (e.g. for taste reasons) food composition for offering theobromine to consumers are fermented, dairy-like, products. Hence, the invention further relates to a fermented food composition comprising from 70 to 99 wt % water (preferably 80-98%), from 0.1 to 10 wt % protein (preferably dairy protein), at least 0.3 wt % lactic acid, and 0.2 to 2 wt % theobromine (herein: % is by weight on the total composition). A fermented food composition herein is a product in which microorganisms are present, either alive or dead, depending on subsequent processing. The fermentation will result in the formation of lactic acid, hence its presence in the composition. For example, "yoghurt" contains in most countries live microorganisms of specific species, but milk, when fermented, and subsequently subject to e.g. an UHT preservation treatment contains mostly dead microorganisms: both are comprised herein by the term fermented (i.e. comprising such microorganisms dead or alive, preferably alive). Preferably, the fermented food compositions as set out herein comprise at least 10 million bacteria (dead or alive, preferably alive) per gram composition, from the group of: *Streptococcus thermophilus, Lactobacillus delbrueckii, Lactobacillus species, Lactococcus species, Bifidobacterium* species, and mixtures thereof. More preferably, such fermented food compositions comprise at least 10 million live bacteria per gram composition, from the group of: *Streptococcus thermophilus* and/or *Lactobacillus delbrueckii* subsp. *bulgaricus*. To achieve both an increase in HDL-C and a decrease in LDL-C, it is preferred that the fermented compositions herein further comprise plant sterols, and preferably in an amount such that theobromine and plant sterols are present in a weight ratio theobromine:plant sterols of from 1:1 to 1:10 (dosing preferably on free plant sterol equivalent). Preferably, the fermented food compositions as set out herein has a pH of between 2 and 7, more preferably between 3 and 5. The dairy protein present preferably comprises dairy protein. A preferred fermented food composition in this context is yoghurt containing the specified amounts of theobromine, and optionally plant sterols. The theobromine in these fermented food compositions may be from cocoa, but does not need to be. Cocoa contains next to e.g. theobromine also polyphenols. E.g. for colour reasons it is preferred that the level of polyphenols (e.g. from cocoa) in the fermented food compositions as set out herein are not more than 5 times the amount of theobromine in the composition, or in other words: the amount of polyphenols (e.g. from cocoa) in the fermented food compositions referred to herein are preferably between 0% and 500% on the weight of theobromine in the fermented food composition, more preferably from 0% to 200% on the weight of theobromine in the fermented food composition, even more preferably from 0% to 50% on the weight of theobromine in the fermented food composition. Epicatechin is a polyphenol present in substantial amounts in cocoa, and e.g. for reasons of taste (e.g. undesired bitterness) it is preferred that the amount of epicatechin (e.g. from cocoa) present in the fermented food compositions as set out herein is not more than the amount of theobromine present in these fermented food compositions, or in other words: the amount of epicatechin (e.g. from cocoa) in the fermented food compositions referred to herein is preferably between 0% and 100% on the weight of theobromine in such fermented food compositions, more preferably from 0% to 50% on the weight of theobromine in such fermented food compositions, even more preferably from 0% to 20% on the weight of theobromine in such fermented food compositions.

The invention further relates to a fermented food composition as set out above, for use in the treatment of increasing HDL-cholesterol in humans and/or for use in the treatment of increasing the ratio HDL-cholesterol/LDL-cholesterol in humans, and/or for use in the treatment of increasing the ratio HDL-cholesterol/non-HDL-cholesterol in humans. For these fermented food compositions in the use specified, it is preferred that the treatment comprises ingestion by a human of from 300 to 2000 mg theobromine per day. Likewise, for these fermented food products in the use specified, it is preferred that the treatment comprises ingestion from 400 to 1800 mg theobromine per day, preferably from 500 to 1500 theobromine mg per day, more preferably from 600 to 1400 mg theobromine per day, even more preferably from 700 to 1300 mg theobromine per day, most preferably from 750 to 1250 mg theobromine per day. Also, for these fermented food products in the use specified, it is preferred that in the treatment, theobromine is ingested for at least 5 days per week for at least 3 weeks, preferably for at least 5 days per week for at least 4 weeks. The theobromine in this may be from cocoa, but does not need to be. Cocoa contains next to e.g. theobromine also polyphenols. E.g. for colour reasons it is preferred that the level of polyphenols (e.g. from cocoa) in the fermented food compositions in the use specified is not more than 5 times the amount of theobromine in the fermented food composition in the use specified, or in other words: the amount of polyphenols (e.g. from cocoa) in the fermented food composition in the use as specified herein are preferably between 0% and 500% on the weight of theobromine in the composition, more preferably from 0% to 200% on the weight of theobromine in the composition, even more preferably from 0% to 50% on the weight of theobromine in the composition. Epicatechin is a polyphenol present in substantial amounts in cocoa, and e.g. for reasons of taste (e.g. undesired bitterness) it is preferred that the amount of epicatechin (e.g. from cocoa) present in these fermented food compositions in the use as specified herein is not more than the amount of theobromine present in these compositions, or in other words: the amount of epicatechin (e.g. from cocoa) in the fermented food compositions in the use as referred to herein is preferably between 0% and 100% on the weight of theobromine in such compositions, more preferably from 0% to 50% on the weight of theobromine in such compositions, even more preferably from 0% to 20% on the weight of theobromine in such compositions.

The invention further relates to a liquid composition comprising water in an amount of more than 70% by weight on the total composition, preferably more than 80% by weight on the total composition and less than 99.8% by weight on the total composition, theobromine in an amount of from 0.3% by weight on the total composition to 2% by weight on the total composition, plant sterols in an amount such that theobromine and plant sterols are present in a weight ratio theobromine:plant sterols of from 1:1 to 1:10 (preferably from 1:2 to 1:5) (dosing preferably on free plant sterol equivalent), for use in the treatment of increasing HDL-cholesterol in humans and/or for use in the treatment of increasing the ratio HDL-cholesterol/LDL-cholesterol in humans, and/or for use in the treatment of increasing the ratio HDL-cholesterol/non-HDL-cholesterol in humans. For these liquid compositions in the use specified, it is preferred that the treatment comprises ingestion by a human of from 300 to 2000 mg theobromine per day. Likewise, for these liquid compositions in the use specified, it is preferred that the treatment comprises ingestion from 400 to 1800 mg theobromine per day, preferably from 500 to 1500 theobromine mg per day, more preferably from 600 to 1400 mg theobromine per day, even more preferably from 700 to 1300 mg theobromine per day, most preferably from 750 to 1250 mg theobromine per day. Also, for these liquid compositions in the use specified, it is preferred that in the treatment, theobromine is ingested for at least 5 days per week for at least 3 weeks, preferably for at least 5 days per week for at least 4 weeks. The theobromine in this may be from cocoa, but does not need to be. Cocoa contains next to e.g. theobromine also polyphenols. E.g. for colour reasons it is preferred that the levels of polyphenols (e.g. from cocoa) in these liquid compositions (including for the use thereof as specified) are not more than 5 times the amount of theobromine in the composition, or in other words: the amount of polyphenols (e.g. from cocoa) in these liquid compositions (including for the use thereof as specified) referred to herein are preferably between 0% and 500% on the weight of theobromine in the liquid composition (including for the use thereof as specified), more preferably from 0% to 200% on the weight of theobromine in the composition, even more preferably from 0% to 50% on the weight of theobromine in the composition. Epicatechin is a polyphenol present in substantial amounts in cocoa, and e.g. for reasons of taste (e.g. undesired bitterness) it is preferred that the amount of epicatechin (e.g. from cocoa) present in these liquid compositions (including for the use thereof as specified) is not more than the amount of theobromine present in these compositions, or in other words: the amount of epicatechin (e.g. from cocoa) in the compositions (including for the use thereof as specified) referred to herein is preferably between 0% and 100% on the weight of theobromine in such compositions, more preferably from 0% to 50% on the weight of theobromine in such compositions, even more preferably from 0% to 20% on the weight of theobromine in such compositions.

Although the compositions as referred to herein, can be made by using high amounts of cocoa, as cocoa contains a small percentage of theobromine, this is not preferred, e.g. due to its strong colour and taste. Hence, it is preferred that the compositions (and their use) according to this invention comprise no or only a low amount of non-fat cocoa solids. More specifically, it is preferred that the compositions (and their use) according to this invention comprise less non-fat cocoa solids than 500% by weight on theobromine (i.e. at maximum 5 times the amount of theobromine in the composition). In other words: the amount of non-fat cocoa solids in the compositions referred to herein are preferably between 0% and 500% on the weight of theobromine in the composition, more preferably from 0% to 200% on the weight of theobromine in the composition, even more preferably from 0% to 50% on the weight of theobromine in the composition. Likewise, the amount of cocoa in the compositions (including their uses) and methods referred to herein is preferably between 0% and 500% on the weight of theobromine in said composition or method, more preferably from 0% to 200% on the weight of theobromine in said composition or method, even more preferably from 0% to 50% on the weight of theobromine in said composition or method. For reasons of e.g. colour and taste, the amount of cocoa-polyphenols in the compositions as set out herein, in the uses, treatments, methods and processes as set out herein is preferably less than 500% (i.e. at maximum 5 times the amount of theobromine in the composition, uses, treatments, methods and processes), more preferably less than 200% by weight on theobromine (in other words: the amount of cocoa polyphenols in the compositions, uses, treatments, methods and processes referred to herein is preferably between 0% and 500%, more preferably between 0% and 200% on the weight of theobromine in the composition, even more preferably from 0% to 50% on the weight of theobromine in the composition, e.g. for ease of product formulation.

In the compositions disclosed herein, their uses, treatments with such compositions, as well as in the methods and processes that use compositions disclosed herein, it is preferred that such compositions comprise less than 0.001% (by weight, based on the total composition) curcumin (and extracts of a plant belonging to the *Curcuma* genus of the Zingiberacea family).

Preferably, in the compositions disclosed herein, their uses, treatments with such compositions, as well as in the methods and processes that use compositions disclosed herein, it is preferred that such compositions comprise no other ingredient or active that has proven and/or suggested to be able to provide an increase in HDL-C in blood or serum in humans (e.g. in an amount of at least 5%), other than theobromine.

Regardless of the composition to be ingested (be it food, be it a medicament, and regardless of a possible combination with other actives known to or believed to influence cholesterol levels in blood), the theobromine in it may preferably be present in an encapsulated form, e.g. microcapsules, optionally included in a food product.

EXAMPLE

Example 1

In a randomised controlled cross-over study with 42 untreated prehypertensive males and females the effect of cocoa-containing drinks either high in polyphenols or high in polyphenols and theobromine was assessed on blood pressure (BP). As a secondary objective the effect of the drinks was assessed on plasma lipid profile.

The subjects consumed for 3 weeks daily (in the morning before breakfast) 200 ml acidified dairy drink as in table 1, with added to that 1) none (control drink), 2) 3.65 g cocoa powder (Acticoa, Barry-Callebaut) containing 500 mg polyphenols and 79 mg theobromine (amount in product specification Acticoa) and 3) 3.65 g cocoa powder containing 500 mg polyphenols and 79 mg theobromine plus added thereto 918 mg pure theobromine (Fagron, Ph.Eur. 5.7) (in total about 1 g theobromine, when the naturally present 79 mg theobromine is added up to the additional 918 mg theobromine). The synthetic theobromine used was: theobromine complying with European Pharmacopeia 5.7, as available from Fagron, Waregem, Belgium.

TABLE 1 composition of the dairy drink (wt % of major components)[1]

|  | placebo | cocoa | cocoa + theobromine |
|---|---|---|---|
| skimmed milk | 30.5 | 30.5 | 30.5 |
| cream | 0.97 | 0.97 | 0.97 |
| Demin. water | 62.9 | 61.5 | 58.7 |
| cocoa powder (Acticoa) | 0 | 1.82 | 1.82 |
| theobromine in NaOH[2] | 0 | 0 | 2.7 |
| sucrose | 3 | 3 | 3 |
| lactic acid | 0.4 | 0.4 | 0.4 |
| flavours | 0.55 | 0 | 0 |
| colourant | 0.09 | 0.08 | 0.07 |
| Total | 98.38 | 98.27 | 98.16 |

[1]200 g dairy product was consumed daily.
[2]Pure theobromine powder was dissolved in 1M NaOH to a stock concentration of approximately 170 mg theobromine per ml. This solution was diluted 38.5 times with the dairy drink (1 part stock solution + 37.5 parts drink).

Inclusion criteria: prehypertensive or grade I hypertensive subjects, age 40-70, with ≤2 additional cardiovascular risk factors, not on active anti-hypertensive treatment. Details are set out in table 2.

TABLE 2

| Parameters | | Mean | SD | 95% CI |
|---|---|---|---|---|
| n | | 42 | | |
| Age | yr | 62 | 4.5 | 60.7-63.5 |
| Male | no (%) | 32 (76%) | | |
| Office SBP | mmHg | 142 | 14.0 | 137-146 |
| Office DBP | mmHg | 84 | 7.9 | 82-87 |
| Length | cm | 177 | 8.1 | 175-180 |
| Weight | kg | 82 | 9.0 | 79-85 |
| BMI | kg/m$^2$ | 25.9 | 2.4 | 25.2-26.7 |
| Fasting glucose | mmol/L | 4.9 | 0.6 | 4.7-5.1 |
| TC | mmol/L | 5.77 | 0.77 | 5.52-6.01 |
| LDL-C | mmol/L | 3.72 | 0.66 | 3.52-3.93 |
| HDL-C | mmol/L | 1.55 | 0.42 | 1.42-1.68 |
| Triglycerides | mmol/L | 1.06 | 0.41 | 0.93-1.19 |
| Smoking | no (%) | 1 (2%) | | |

Methodology

Venous blood samples were drawn from the antecubital vein in EDTA containing tubes in fasting condition (morning, before breakfast) for lipid profile (HDL-C, LDL-C, total cholesterol, triglycerides, HDL-C being herein high density lipoprotein cholesterol, and LDL-C herein being low density lipoprotein cholesterol). The blood samples were taken at baseline and were repeated after the end of each treatment period. All measurements were done with standard laboratory techniques.

Descriptive Statistics

Plasma lipid outcomes were done in the Per Protocol population. Linear mixed models were performed using compound symmetry repeated covariance type with treatment as a fixed factor and with baseline parameters as a covariate. We performed pairwise comparisons with no adjustment for multiple testing to assess differences between placebo and the two treatment arms. A 2 sided p-value<0.05 was considered significant.

Results 85 subjects were screened and 42 of them were found eligible to enter the study. The population characteristics at baseline were as follows (average values with between brackets standard deviation): 32 males (76%), age 62 (4.5), office SBP 142 (14) and DBP 84 (8), BMI 25.9 (2.4), total cholesterol 5.77 (0.77), 2% smokers. Data from four subjects were discarded for various reasons (e.g. arrhythmia, holiday, BP measurement failure). The remaining population was defined as the Per Protocol population.

Compliance was >99% as estimated from counting returned empty bottles.

The results are set out in table 3 and 4.

In table 3: tests of fixed effects and mean estimates, standard error (SE), 95% confidence interval (95% CI), and significant difference between interventions of plasma total cholesterol, HDL-C and LDL-C. Baseline values were included as covariable.

TABLE 3

| Parameter | Covariable | Treatment | Mean | SE | 95% CI | p value |
|---|---|---|---|---|---|---|
| Total cholesterol (mM) | Baseline Total cholesterol | Placebo | 5.61 | 0.10 | 5.40-5.81 | 0.46 |
| | | Cocoa | 5.68 | 0.10 | 5.48-5.88 | |
| | | Theobromine* | 5.72 | 0.10 | 5.52-5.92 | |
| HDL (mM) | Baseline HDL | Placebo | 1.55 | 0.03 | 1.48-1.62 | >0.001 |
| | | Cocoa | 1.60 | 0.03 | 1.54-1.67 | |
| | | Theobromine* | 1.74 | 0.03 | 1.67-1.81 | |

TABLE 3-continued

| Parameter | Covariable | Treatment | Mean | SE | 95% CI | p value |
|---|---|---|---|---|---|---|
| LDL (mM) | Baseline LDL | Placebo | 3.55 | 0.08 | 3.39-3.71 | 0.35 |
| | | Cocoa | 3.58 | 0.08 | 3.42-3.74 | |
| | | Theobromine* | 3.47 | 0.08 | 3.31-3.64 | |

*Cocoa with pure theobromine added.

In table 4: pairwise comparisons between placebo and cocoa and cocoa plus theobromine interventions of total cholesterol, HDL-C and LDL-C plasma values.

TABLE 4

| Parameter | treatment A | treatment B | Change (A − B) | SE | 95% CI | p value |
|---|---|---|---|---|---|---|
| Total cholesterol (mM) | Placebo | Cocoa | 0.072 | 0.09 | −0.11-0.25 | 0.43 |
| | | Theobromine* | 0.113 | 0.09 | −0.07-0.29 | 0.22 |
| HDL-C (mM) | Placebo | Cocoa | 0.050 | 0.03 | −0.01-0.11 | 0.12 |
| | | Theobromine* | 0.183 | 0.03 | 0.12-0.25 | 0.000 |
| LDL-C (mM) | Placebo | Cocoa | 0.033 | 0.08 | −0.12-0.18 | 0.66 |
| | | Theobromine* | −0.073 | 0.08 | −0.22-0.08 | 0.33 |

*Cocoa with pure theobromine added.

Thus, plasma HDL-C increased significantly in the cocoa-theobromine intervention from 1.55 (placebo) and 1.60 (cocoa) to 1.74 mM (cocoa+theobromine). Compared to placebo this is a 12% increase and compared to cocoa a 9% increase. Plasma LDL-C decreased slightly, which had an additional positive effect on the HDL-C:LDL-C ratio, increasing from 0.44 (placebo) and 0.45 (cocoa) to 0.50 (cocoa+theobromine).

Conclusion

Consumption of theobromine increases plasma HDL-C and HDLC:LDL-C ratio in humans.

Example 2

In a randomized controlled intervention study with 153 healthy males and females the effect of drinks containing cocoa, added theobromine or a combination of cocoa and added theobromine was assessed on HDL cholesterol (HDL-C). As a secondary objective the effect of the various drinks on total cholesterol (TC), LDL cholesterol (LDL-C), Triglycerides (TG) and blood pressure (BP) was assessed.

The study had a bi-centric, double-blind, randomized, placebo-controlled, 2 by 2 full factorial parallel design. After a run-in period of 2 weeks the subjects consumed for 4 weeks daily (in the morning one hour before breakfast) 200 ml acidified dairy drink as in table 5, with added to that 1) none (control drink), 2) 5.9 g cocoa powder (Acticoa, Barry-Callebaut) containing about 500 mg polyphenols and 150 mg theobromine 3) about 850 mg synthetic theobromine (Fagron) and 4) 5.9 g cocoa powder containing 500 mg polyphenols and 150 mg theobromine plus added thereto about 850 mg synthetic theobromine (Fagron) (in total about 1 g theobromine). The synthetic theobromine used was: theobromine complying with European Pharmacopeia 5.7, as available from Fagron, Waregem, Belgium.

For preparing the test products containing theobromine, theobromine was dissolved in a 1 M NaOH solution to create a theobromine stock solution, containing approximately 170 mg/ml of thebromine. The various drinks used in the trial have been made using the following processing:

- mixing of the pectin with all of the sugar
- dispersing the pectin/sugar mix with part of the demi water at 80° C. to prepare a pectin slurry
- dissolving smp in the remainder of the demi water at a temperature of 40° C.
- adding the cream
- adding the xanthan gum under vigorous mixing for 15 minutes
- adding the pectin slurry
- adding sucralose
- (depending on the drink: adding the cacao slowly under vigorous mixing)
- (depending on the drink: adding the theobromine solution)
- adding the sunflower oil
- adding the flavours and colorants
- acidifying the premix with lactic acid until pH 4.2

The process to prepare bottles containing the drink so prepared in a pasteurised form further contained the step of homogenisation after pasteurisation.

TABLE 5

Composition of the dairy drink (wt % of major components)[1]

| | placebo | cocoa | theobromine | cocoa + theobromine |
|---|---|---|---|---|
| skimmed milk powder | 3.06 | 3.06 | 3.06 | 3.06 |
| cream | 0.97 | 0.97 | 0.97 | 0.97 |
| Demineralised water | 91.85 | 88.10 | 88.18 | 84.8 |
| cocoa powder (Acticoa) | 0 | 2.9 | 0 | 2.9 |
| theobromine in NaOH[2] (solution) | 0 | 0 | 3.06 | 3.06 |
| sucrose | 2.0 | 3.0 | 2.0 | 3.0 |
| lactic acid | 0.4 | 0.4 | 0.65 | 0.65 |
| flavours | 0.5 | 0 | 0.5 | 0 |
| colorants | 0.08 | 0.06 | 0.08 | 0.06 |
| HM pectin | 0.4 | 0.32 | 0.40 | 0.4 |
| xanthan gum | 0.1 | 0.08 | 0.10 | 0.1 |
| sunflour oil | 1.0 | 1.0 | 1.0 | 1.0 |
| sucralose | 0.01 | 0.01 | 0.01 | 0.01 |
| Total | 100.37 | 99.9 | 100.01 | 100.01 |

[1]200 ml dairy product was consumed daily.
[2]Pure theobromine powder was dissolved in 1M NaOH to a stock concentration of approximately 170 mg theobromine per ml. This solution was then diluted with the dairy drink.

Inclusion criteria: generally healthy men and pre-menopausal women, age 40-70, with a 10-year risk of developing CHD<10%, not on active cholesterol-lowering or anti-hypertensive treatment and non-smoking. Details of the subject characteristics are set out in table 6.

TABLE 6

Subject characteristics

| Parameters | | Mean | SD | range |
|---|---|---|---|---|
| n | | 153 | | |
| Age | yr | 54.9 | 8.5 | 40-70 |
| Male | no (%) | 77 (50.3%) | | |

TABLE 6-continued

Subject characteristics

| Parameters | | Mean | SD | range |
|---|---|---|---|---|
| Office SBP | mmHg | 124.0 | 13.3 | 94.0-166.0 |
| Office DBP | mmHg | 80.9 | 9.0 | 59.0-112.0 |
| Length | cm | 168.8 | 9.0 | 149-191 |
| Weight | kg | 70.0 | 12.1 | 46.0-100.7 |
| BMI | kg/m$^2$ | 24.4 | 2.8 | 18.8-30.8 |
| Fasting blood glucose | mmol/L | 5.08 | 0.50 | 3.70-6.33 |
| TC | mmol/L | 5.98 | 1.05 | 3.1-8.26 |
| LDL-C | mmol/L | 3.76 | 0.95 | 1.29-6.24 |
| HDL-C | mmol/L | 1.72 | 0.50 | 0.93-3.1 |
| Triglycerides | mmol/L | 1.12 | 0.65 | 0.32-4.97 |

Methodology

Venous blood samples were drawn from the antecubital vein in SST II advance BD tubes in fasting condition (morning, before breakfast) for blood lipid profile (HDL-C, LDL-C, total cholesterol (TC), triglycerides, HDL-C being herein high density lipoprotein cholesterol, and LDL-C herein being low density lipoprotein cholesterol). The blood samples were taken twice at baseline and were repeated twice after the end of the intervention period. All measurements were done with standard laboratory techniques.

Descriptive Statistics

Serum lipid outcomes were done in the Intention to treat (ITT) and Per Protocol (PP) population.

The statistical analysis was done according to a full 2×2 factorial design including interaction of theobromine and cocoa. Gender within treatment and baseline blood lipids were included in the model as covariates. A 2 sided p-value<0.05 was considered significant.

Results 203 subjects were screened and 153 of them were found eligible to enter the study. The population characteristics at baseline were as follows (average values with between brackets standard deviation): 77 males (50%), age 54.9 yrs (8.5), weight 70.0 kg (12.1), height 168.8 cm (9.0), BMI 24.4 (2.8), total cholesterol 5.98 mmol/L (1.05), SBP 124 mmHg (13.3) and DBP 80.9 mmHg (9.0). Ten people withdrew from the study prematurely; data from nine more subjects were discarded from the PP analysis as they lost or gained more than 2 kg body weight during the study, which could have had an impact on the blood lipid profile. Reported are the results of the ITT population (n=143) as it showed similar results as the PP analysis.

Compliance was >99.7% as estimated from counting returned empty bottles and consumption diaries. The results are set out in table 7 and 8.

Table 7: Tests of fixed effects and mean estimates, standard error (SE), 95% confidence interval (95% CI), and significant difference between interventions of plasma total cholesterol, HDL-C and LDL-C, HDL/non-HDL-cholesterol ratio, HDL/LDL-cholesterol ratio, triglycerides, diastolic and systolic blood pressure. Baseline values and gender were included as co-variables.

TABLE 7

| Parameter | Covariable | Treatment | Mean | SE | 95% CI | p value |
|---|---|---|---|---|---|---|
| Total cholesterol (mmol/L) | Baseline Total cholesterol Gender | Placebo | 5.86 | 0.07 | 5.73-6.00 | 0.81 |
| | | Cocoa | 5.89 | 0.07 | 5.75-6.02 | |
| | | Theobromine | 5.82 | 0.07 | 5.69-5.96 | |
| | | TB + C | 5.82 | 0.07 | 5.67-5.96 | |
| HDL-C (mmol/L) | Baseline HDL Gender | Placebo | 1.60 | 0.03 | 1.54-1.65 | <0.001 |
| | | Cocoa | 1.66 | 0.03 | 1.60-1.71 | |
| | | Theobromine | 1.75 | 0.03 | 1.70-1.81 | |
| | | TB + C | 1.87 | 0.03 | 1.81-1.93 | |
| LDL-C (mmol/L) | Baseline LDL Gender | Placebo | 3.48 | 0.05 | 3.38-3.58 | <0.05 |
| | | Cocoa | 3.46 | 0.05 | 3.35-3.56 | |
| | | Theobromine | 3.30 | 0.05 | 3.19-3.40 | |
| | | TB + C | 3.27 | 0.06 | 3.16-3.39 | |
| HDL-C/non-HDL-C ratio | Baseline ratio Gender | Placebo | 0.38 | 0.02* | 0.36-0.39 | <0.0001 |
| | | Cocoa | 0.39 | 0.02* | 0.38-0.41 | |
| | | Theobromine | 0.43 | 0.02* | 0.41-0.44 | |
| | | TB + C | 0.46 | 0.02* | 0.44-0.48 | |
| HDL-C/LDL-C ratio | Baseline ratio Gender | Placebo | 0.47 | 0.02* | 0.45-0.48 | <0.0001 |
| | | Cocoa | 0.48 | 0.02* | 0.46-0.50 | |
| | | Theobromine | 0.52 | 0.02* | 0.50-0.54 | |
| | | TB + C | 0.55 | 0.02* | 0.53-0.57 | |
| Triglyceride (mmol/L) | Baseline triglyceride Gender | Placebo | 1.03 | 0.04* | 0.96-1.10 | 0.48 |
| | | Cocoa | 1.01 | 0.04* | 0.95-1.09 | |
| | | Theobromine | 1.05 | 0.03* | 0.98-1.12 | |
| | | TB + C | 0.94 | 0.04* | 0.87-1.01 | |
| DBP (mm Hg) | Baseline DBP Gender | Placebo | 75.3 | 0.95 | 73.3-77.2 | 0.99 |
| | | Cocoa | 74.4 | 0.97 | 72.4-76.4 | |
| | | Theobromine | 75.0 | 0.95 | 73.1-77.0 | |
| | | TB + C | 76.3 | 1.03 | 74.2-78.5 | |
| SBP (mm Hg) | Baseline SBP Gender | Placebo | 118.7 | 1.81 | 115.0-122.4 | 0.47 |
| | | Cocoa | 117.7 | 1.88 | 113.9-121.6 | |
| | | Theobromine | 121.2 | 1.79 | 117.6-124.9 | |
| | | TB + C | 121.8 | 1.96 | 117.8-125.8 | |

*SE are on log-transformed data.

TABLE 8

Pair-wise comparisons between placebo and cocoa and cocoa plus theobromine interventions of total cholesterol, HDL-C and LDL-C, HDL/non-HDL-cholesterol ratio, HDL/LDL-cholesterol ratio, tryglycerides, diastolic and systolic blood pressure.

| Parameter | treatment A | treatment B | Change (A − B) | SE | 95% CI | p value |
|---|---|---|---|---|---|---|
| Total cholesterol (mmol/L) | Placebo | Cocoa | 0.027 | 0.10 | −0.16-0.22 | 0.77 |
| | | Theobromine | −0.038 | 0.10 | −0.23-0.15 | 0.70 |
| | | TB + C | −0.046 | 0.10 | −0.25-0.15 | 0.65 |
| HDL-C (mmol/L) | Placebo | Cocoa | 0.061 | 0.04 | −0.02-0.14 | 0.13 |
| | | Theobromine | 0.159 | 0.04 | 0.08-0.24 | <0.0001 |
| | | TB + C | 0.272 | 0.04 | 0.19-0.35 | <0.0001 |
| LDL-C (mmol/L) | Placebo | Cocoa | −0.022 | 0.07 | −0.17-0.12 | 0.76 |
| | | Theobromine | −0.184 | 0.08 | −0.33--0.04 | 0.02 |
| | | TB + C | −0.207 | 0.08 | −0.36--0.05 | <0.01 |
| HDL-C/non-HDL-C ratio | Placebo | Cocoa | 0.040 | 0.03* | −0.02-0.10 | 0.17 |
| | | Theobromine | 0.126 | 0.03* | 0.07-0.18 | <0.0001 |
| | | TB + C | 0.198 | 0.03* | 0.14-0.26 | <0.0001 |
| HDL-C/LDL_c ratio | Placebo | Cocoa | 0.033 | 0.03* | −0.02-0.08 | 0.20 |
| | | Theobromine | 0.117 | 0.03* | 0.07-0.17 | <0.0001 |
| | | TB + C | 0.165 | 0.03* | 0.11-0.22 | <0.0001 |
| Triglycerides (mmol/L) | Placebo | Cocoa | −0.013 | 0.05 | −0.11-0.08 | 0.79 |
| | | Theobromine | 0.018 | 0.05 | −0.08-0.12 | 0.72 |
| | | TB + C | −0.092 | 0.05 | −0.20-0.01 | 0.08 |
| DBP (mm Hg) | Placebo | Cocoa | −0.84 | 1.39 | −3.69-2.01 | 0.55 |
| | | Theobromine | −0.20 | 1.35 | −2.97-2.57 | 0.88 |
| | | TB + C | 1.10 | 1.39 | −1.77-3.96 | 0.44 |
| SBP (mm Hg) | Placebo | Cocoa | −0.95 | 2.71 | −6.52-4.63 | 0.73 |
| | | Theobromine | 2.55 | 2.55 | −2.69-7.80 | 0.33 |
| | | TB + C | 3.12 | 2.64 | −2.31-8.55 | 0.25 |

* SE are on logtransformed data.

The analysis showed that theobromine (TB) alone had a significant effect on HDL-C levels resulting in an increase of 0.16 mmol/L which is about a 10% increase compared to placebo (p<0.0001). The combination of theobromine and cocoa (TB+C) significantly increased the HDL-C levels by 0.27 mmol/L, i.e. about a 17% increase compared to placebo (p<0.0001). This increase is more than the separate effects of theobromine and cocoa combined, although no significant interaction was found (+0.05 mmol/L, p=0.3735). Cocoa alone did not significantly increase HDL-C levels (+0.06 mmol/L, p=0.1288).

A significant increase in ApoA1 concentrations, the main apoprotein found in HDL particles, was seen with theobromine alone (+0.11, p<0.0001) and the combination of theobromine and cocoa. No significant interaction effect was found.

Serum LDL-C decreased slightly by 0.18 mmol/L upon treatment with theobromine alone, i.e. a decrease of about 5% compared to placebo. This consequently had an additional positive effect on the HDL-C:LDL-C and HDL-C:non-HDL-C ratios. Theobromine alone significantly increased the HDL-C:LDL-C ratio by 0.12 (p<0.0001) and the HDL-C:non-HDL-C ratio by 0.13 (p<0.0001).

No effect on total cholesterol (p=0.81) and triglycerides (p=0.48) was found.

Theobromine alone showed no significant effect on blood pressure, neither on systolic BP (SBP+2.55 mmHg vs control; p=0.33) nor on diastolic BP (DBP−0.20 mmHg vs. control; p=0.88). Cocoa alone and the combination of theobromine and cocoa did not have an effect on BP, either.

Conclusion

Daily intake of 850 mg theobromine (TB) for 4 weeks significantly increases HDL-C compared to placebo. The effect is attributable to theobromine; there is no significant interaction effect with cocoa.

Example 3a

To a commercial 35% low fat spread (product as available in the Netherlands under the trademark Becel Light) theobromine (not the salt form, contrary to examples 1 and 2) was added (1.65% and 3.30%), mixed with a spoon and judged on appearance. White theobromine particles were visible in both spreads.

Example 3b

Two plant-sterol ester containing spreads were prepared on lab scale with a microvotator, one reference and one with theobromine in a concentration of 1.65 wt % (500 mg per serving of 30 gram). The composition is in table 9 below.

TABLE 9

| composition | |
|---|---|
| Ingredient | Amount (wt %) |
| Refined sunflower oil | 24.1% |
| Plant sterol esters | 12.5% |
| Palm oil fraction and palm kernel oil (chemically interesterified) | 5.4% |
| Emulsifier (DIMODAN HP) | 0.3% |
| Sunflower lecithin (SUNLEC M) | 0.1% |
| Demineralised water (Millipore) | 52.9% |
| Tapioca starch | 2.5% |
| Theobromine | 1.7% |
| Butter milk powder | 0.3% |
| Potassium sorbate | 0.1% |

Processing was done in a conventional way for making a spread using a microvotator, with the exception that the theobromine (not the salt form, unlike examples 1 and 2) was added to the water phase and mixed well for 3 minutes with an ultra turrax mixer at 6000 rpm.

In the resulting product there were no particles visible in this spread with theobromine and there was no effect on the colour of the spread when compared to the one without.

Example 3c

A potassium-enriched low fat spread was produced using a standard formulation (as in table 10), but without colour and flavour. To this, per 20 g spread was added 0.5 g theobromine.

TABLE 10

| composition | |
|---|---|
| Ingredient | Amount (wt %) |
| Refined sunflower oil | 31.6% |
| Palm oil fraction and palm kernel oil (chemically interesterified) | 5.5% |
| Emulsifier (DIMODAN HP) | 0.2% |
| Sunflower lecithin (SUNLEC M) | 0.1% |
| Demineralised water (Millipore) | 45.9% |
| Theobromine | 2.5% |
| Polyglycerol polyricinoleate | 0.4% |
| Potassium sorbate | 0.1% |
| Potassium gluconate | 13.6% |

The invention claimed is:

1. A method for increasing HDL-cholesterol in a human in need of treatment of increasing HDL-cholesterol, said method comprising:
    administering to the human 300 to 2000 mg theobromine per day, wherein the theobromine is administered in an edible emulsion comprising, by weight, 20% to 85% of oil, 15% to 80% water and 0.5% to 10% theobromine,
    wherein at least a plant polyphenol is present in the emulsion, and the amount of the plant polyphenol is up to 500% based on the weight of the theobromine,
    wherein the emulsion further comprises a plant sterol, and a weight ratio of the theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in HDL-cholesterol in humans in blood and/or serum is at least 5%.

2. The method of claim 1, wherein said emulsion comprising, by weight, 2%-20% of the plant sterol.

3. The method of claim 1, wherein the amount of the plant polyphenol in said emulsion is between 0% and 50% on the weight of the theobromine in the emulsion.

4. The method of claim 1, wherein in the edible emulsion the water is in the amount of 70% by weight, the theobromine is in the amount of from 0.5% to 2% by weight, and the plant sterol and the theobromine are present in a weight ratio from 1:1 to 1:10.

5. The method of claim 4, wherein the composition comprises from 85 to 99% by weight on the total composition of water.

6. The method of claim 4, wherein the composition comprises from 0.4 to 1.5% by weight on the total composition of theobromine.

7. The method of claim 1, wherein the administering step comprises administering an edible emulsion comprising theobromine, EPA, and DHA, wherein the weight ratio of theobromine:EPA and DHA combined is from 1:4 to 1:0.3.

8. The method of claim 1, wherein the edible emulsion further comprising a statin, wherein the theobromine and the statin are present in a weight ratio from 200:1 to 5:1.

9. The method of claim 1, wherein the edible emulsion further comprising a statin, wherein the theobromine and the statin are present, in a weight ratio from 100:1 to 10:1.

10. The method of claim 1, wherein epicatechin is present in the emulsion and the weight ratio of the epicatechin: the theobromine is u 0.2:1.

11. The method of claim 1, wherein the emulsion comprising a statin selected from the group consisting of atorvastatin, fluvastatin, lovastatin, pitavastatin, pravastatin, rosuvastatin, simvastatin, cerivastatin, mevastatin, and mixtures thereof.

12. The method of claim 1, wherein administering to the human 750 to 1250 mg theobromine per day, and the administering step is performed for at least 5 days per week for at least 3 weeks.

13. A method for increasing the ratio HDL-cholesterol LDL-cholesterol in a human in need of treatment for improving blood lipids and/or blood lipids profile, said method comprising:
    administering to the human 300 to 2000 mg theobromine per day,
    wherein the theobromine is administered in an edible emulsion comprising, by weight, 20% to 85% of oil, 15% to 80% water, and 0.5% to 10% theobromine,
    wherein at least a plant polyphenol is present in the emulsion, and the amount of the plant polyphenol is up to 500% based on the weight of the theobromine,
    wherein the emulsion further comprises a plant sterol, and a weight ratio of the theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in the ratio HDL-cholesterol LDL-cholesterol in humans in blood and/or serum is at least 5%.

14. A method for increasing the ratio HDL-cholesterol/non-HDL-cholesterol in a human in need of treatment for improving blood lipids and/or blood lipids profile, said method comprising:
    administering to the human 300 to 2000 mg theobromine per day,
    wherein the theobromine is administered in an edible emulsion comprising, by weight, 20% to 85% of oil, 15% to 80% water, and 0.5% to 10% theobromine,
    wherein at least a plant polyphenol is present in the emulsion, and the amount of the plant polyphenol is up to 500% based on the weight of the theobromine,
    wherein the emulsion further comprises a plant sterol, and a weight ratio of the theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in the ratio HDL-cholesterol/non-HDL-cholesterol in humans in blood and/or serum is at least 5%.

15. A method for increasing HDL-cholesterol in a human in need of treatment of increasing HDL-cholesterol and having HDL-cholesterol level of 1.55 mmol/L or less, said method comprising:
    administering to the human 300 to 2000 mg theobromine per day,
    wherein the theobromine is administered in an edible emulsion comprising, by weight, 20% to 85% of oil, 15% to 80% water, and 0.5% to 10% theobromine,
    wherein the emulsion further comprises a plant sterol, and a weight ratio of theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in HDL-cholesterol in humans in blood and/or serum is at least 5%.

16. A method for increasing the ratio HDL-cholesterol/LDL-cholesterol in a human in need of treatment for improving blood lipids and/or blood lipids profile and having an HDL-cholesterol level of 1.55 mmol/L or less, said method comprising:
    administering to the human 300 to 2000 mg theobromine per day,
    wherein the theobromine is administered in an edible emulsion comprising, by weight, 20% to 85% of oil, 15% to 80% water, and 0.5% to 10% theobromine,
    wherein the emulsion further comprises a plant sterol, and a weight ratio of theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in the ratio HDL-cholesterol LDL-cholesterol in humans in blood and/or serum is at least 5%.

17. A method for increasing the ratio HDL-cholesterol/non-HDL-cholesterol in a human in need of treatment for improving blood lipids and/or blood lipids profile and having an HDL-cholesterol level of 1.55 mmol/L or less, said method comprising:
    administering to the human 300 to 2000 mg theobromine per day,
    wherein the theobromine is administered in an edible emulsion comprising, by weight, 20% to 85% of oil, 15% to 80% water, and 0.5% to 10% theobromine,
    wherein the emulsion further comprises a plant sterol, and a weight ratio of theobromine: the plant sterol is from 0.3:1 to 1:1,
    wherein the emulsion further comprises EPA and DHA, and a weight ratio of the theobromine: the combined weight of EPA and DHA is from 1:2 to 1:0.5, and
    wherein the increase in the ratio HDL-cholesterol/non-HDL-cholesterol in humans in blood and/or serum is at least 5%.

* * * * *